(12) United States Patent
Parrini et al.

(10) Patent No.: US 12,193,859 B2
(45) Date of Patent: Jan. 14, 2025

(54) SYSTEM FOR PERFORMING ROBOTIC SURGERY

(71) Applicant: Epica International, Inc., San Clemente, CA (US)

(72) Inventors: Gianluca Parrini, Cascina (IT); Luca Ferretti, Pisa (IT); Luca Bosio, Pisa (IT); Frank D'Amelio, San Clemente, CA (US); Leonardo Manetti, Montevarchi (IT); Damiano Fortuna, Rignano Sull'Arno (IT)

(73) Assignee: EPICA INTERNATIONAL, INC., San Clemente, CA (US)

( * ) Notice: Subject to any disclaimer, the term of this patent is extended or adjusted under 35 U.S.C. 154(b) by 46 days.

(21) Appl. No.: 16/402,002

(22) Filed: May 2, 2019

(65) Prior Publication Data

US 2019/0336093 A1  Nov. 7, 2019

Related U.S. Application Data

(60) Provisional application No. 62/666,035, filed on May 2, 2018.

(51) Int. Cl.
*A61B 6/00* (2024.01)
*A61B 6/03* (2006.01)
(Continued)

(52) U.S. Cl.
CPC .............. *A61B 6/4435* (2013.01); *A61B 6/04* (2013.01); *A61B 6/4458* (2013.01); *A61B 34/30* (2016.02);
(Continued)

(58) Field of Classification Search
None
See application file for complete search history.

(56) References Cited

U.S. PATENT DOCUMENTS 4,645,933 A * 2/1987 Gambini .............. A61B 6/4405
                                                250/363.05
6,035,228 A    3/2000 Yanof et al.
(Continued)

FOREIGN PATENT DOCUMENTS

DE  102008019646 A1  10/2009
EP     0919203 A2   6/1999
(Continued)

OTHER PUBLICATIONS

International Search Report and Written Opinion dated Oct. 2, 2019 issued in PCT/US2019/030462.
(Continued)

*Primary Examiner* — Katherine L Fernandez
*Assistant Examiner* — Farouk A Bruce
(74) *Attorney, Agent, or Firm* — STEPTOE LLP; Carl B. Wischhusen

(57) ABSTRACT

A system for performing robotic surgery on a patient disposed on a bed includes a gantry comprising a computed tomography (CT) diagnostic device, a platform supporting the gantry, and a robotic arm assembly attached to the platform. The gantry slides along the platform via a first carriage to allow entry of at least part of the patient into the bore of the CT device. The robotic arm assembly is attached to the platform via a pivot arm and a second carriage to allow the assembly to slide along the platform to enable surgery to be performed on the patient. The pivot arm is substantially parallel to the upper surface of the platform.

2 Claims, 22 Drawing Sheets

(51) Int. Cl.
*A61B 6/04* (2006.01)
*A61B 34/30* (2016.01)

(52) U.S. Cl.
CPC ......... *A61B 6/035* (2013.01); *A61B 2034/302* (2016.02)

(56) References Cited

U.S. PATENT DOCUMENTS

| | | | |
|---|---|---|---|
| 6,505,065 B1 | 1/2003 | Yanof et al. | |
| 2007/0165786 A1* | 7/2007 | Grasser | A61B 6/4458 378/194 |
| 2014/0188132 A1* | 7/2014 | Kang | A61B 34/30 606/130 |
| 2016/0008078 A1 | 1/2016 | Azizian et al. | |
| 2016/0249990 A1 | 9/2016 | Glozman et al. | |
| 2016/0302871 A1 | 10/2016 | Gregerson et al. | |
| 2018/0000454 A1* | 1/2018 | Senn | A61B 8/481 |
| 2018/0207794 A1* | 7/2018 | Sebring | B25J 9/0018 |
| 2019/0038240 A1* | 2/2019 | Fortuna | A61B 34/30 |
| 2019/0216550 A1* | 7/2019 | Eyre | A61G 13/08 |
| 2019/0216555 A1* | 7/2019 | DiMaio | A61B 34/00 |
| 2019/0231460 A1* | 8/2019 | DiMaio | B25J 9/1684 |
| 2019/0380669 A1* | 12/2019 | Uher | A61N 5/1083 |

FOREIGN PATENT DOCUMENTS

| | | |
|---|---|---|
| EP | 1095628 A2 | 5/2001 |
| WO | 2018049196 A1 | 3/2010 |
| WO | 2016/168671 A2 | 10/2016 |
| WO | 2017134546 A2 | 8/2017 |

OTHER PUBLICATIONS

Extended European Search Report from EP Application No. 19797025. 4, Dec. 14, 2021, 10 pages.
Communication under Rule 71(3) EPC from European Patent Application No. 19797025.4, Jun. 18, 2024, 10 pages.

* cited by examiner

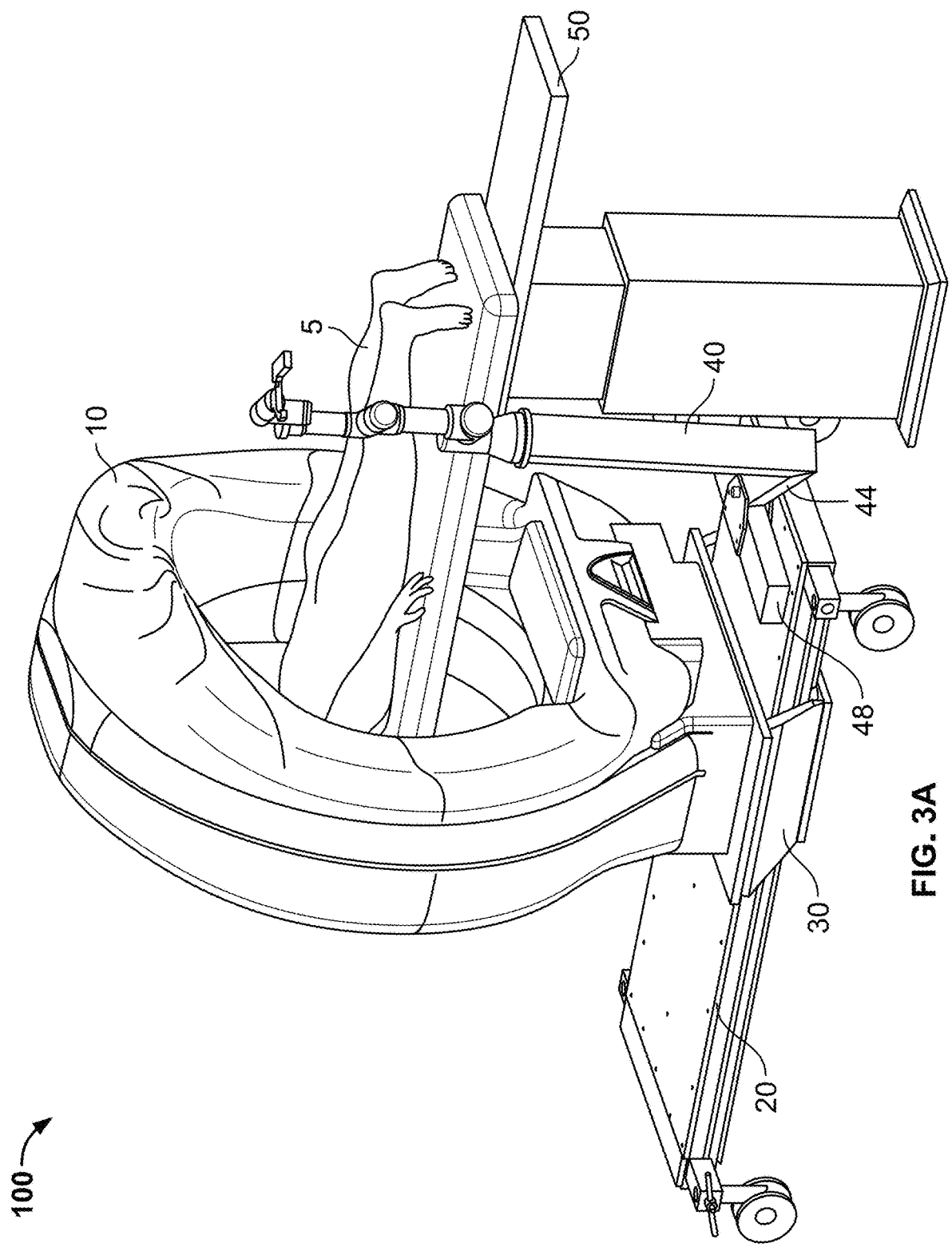

SYSTEM FOR PERFORMING ROBOTIC SURGERY

CLAIM OF PRIORITY

This application claims priority from U.S. Provisional Application No. 62/666,035, filed on May 2, 2018, which is incorporated by reference in its entirety.

BACKGROUND

X-ray computed tomography (CT) may be used to scan and image an area of a patient prior to or during surgery. Such imaging has recently been supplemented with a robotic arm to perform or assist with the surgery. The arrangement of the gantry and the robotic arm may make it difficult in some situations to perform surgery on the patient.

BRIEF DESCRIPTION OF THE DRAWINGS

FIGS. 3A-3C show uses of the system of FIG. 1A during thoracic operations, according to embodiments of the invention;

Figure 1A:
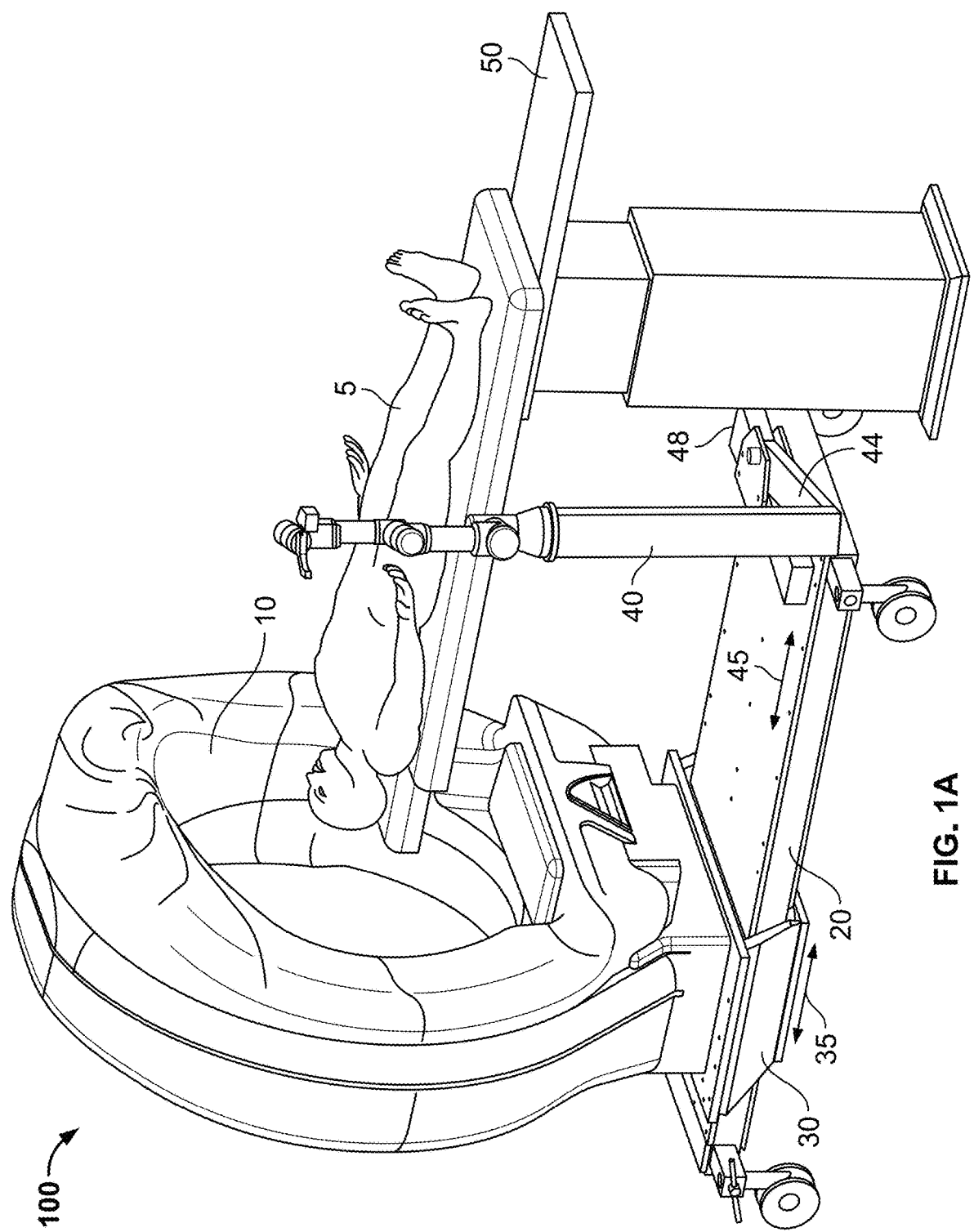
FIG. 1A is a system for performing robotic surgery, according to an embodiment of the present invention.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

The inventors have developed a system that allows a surgeon to operate on a variety of locations on a patient, including left and right thoracic cavity; left and right abdominal cavity; left, right, and center of the brain; and areas of the neck. The system includes a gantry including a CT, a platform supporting the gantry, and a robotic arm assembly attached to the platform or the gantry via a pivot arm. Depending on the bore diameter of the gantry, various embodiments have been made to allow the robotic arm to access different parts of the body.

Reference is now made to FIG. 1A, which shows a system 100 for performing robotic surgery, according to an embodiment of the present invention. System 100 includes gantry 10, which contains within it a CT scanning and imaging device, platform 20 that supports gantry 10, and robotic arm assembly 40. Gantry 10 may move along direction 35 via carriage 30 in order to engage and disengage the CT with patient 5, who is disposed on bed 50. Patient 5 may be human or may be an animal, in the event that the CT device is used for veterinary purposes. Gantry 10 may have a bore diameter of 95 cm or more to allow patient 5 to have full body access to the CT device. Bed 50 may be a poly-articulated operating bed, e.g., the TruSystem® 7500 Hybrid Operating Room Table manufactured by Trumpf Medical, of Germany, a subsidiary of Hill-Rom Holdings, Inc. Other operating beds may also be used, including those that are not fixed in place (e.g., those with wheels that lock). An example of a radiological bed has been described in PCT International Publication No. WO 2018/047052, "Radiological bed," published Mar. 15, 2018, and subject to an assignment to the applicant of this application or to an affiliate of the applicant, the entirety of which is incorporated herein by reference to the extent applicable. Platform 20 may have wheels in order to move the whole system if needed, for example to allow for more space for surgical staff to perform surgery. Robotic arm assembly 40 may be attached via pivot arm 44 to a second carriage 48, which is attached to platform 20 and may move along direction 45.

Figure 1B:
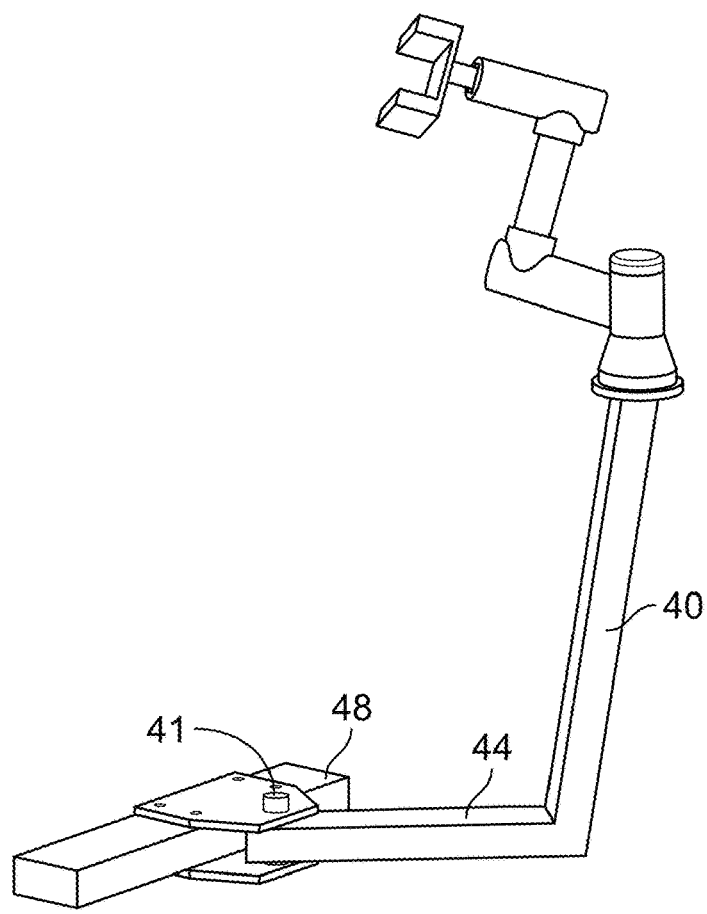
FIGS. 1B and 1C are more detailed diagrams of the robotic arm assembly of the system of FIG. 1A, according to embodiments of the present invention.
Figure 1C:
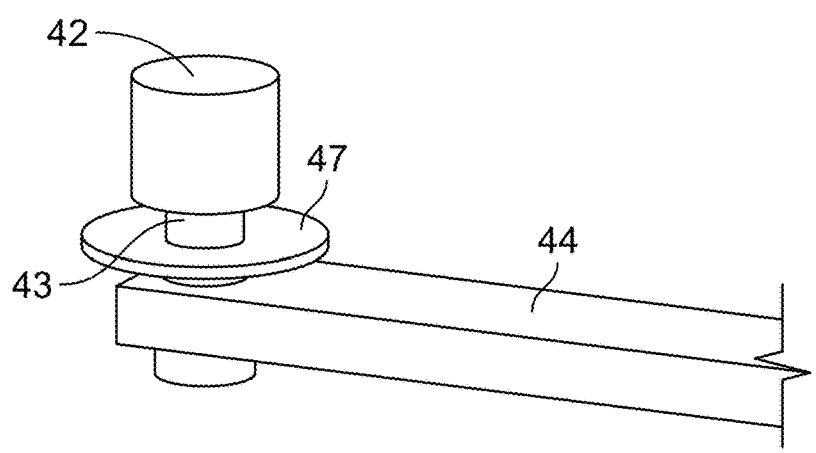

Pivot arm 44 is substantially parallel to the upper surface of platform 20. Pivot arm 44 allows robotic arm assembly 40 to be placed in multiple positions to allow better access to patient 5. As shown in FIG. 1B, pivot arm 44 may be attached to second carriage 48 via pivot 41, which may be pivoted by a surgeon. As shown in FIG. 1C, pivot 41 may be replaced by motor shaft 43 attached to motor 42, which may be a stepper motor, which may allow for more precise positioning and control of robotic arm assembly 40 around the pivot point, including to lock pivot arm 44 in place. The pivot/motor assembly may also include optical encoder 47 and multiple solenoids (not shown), brushless torque actuators (BTA), or other alternative means, such as ratcheting devices, or gear arrangements, to enhance the precision, control, and locking abilities. The motion of second carriage 48 along direction 45 may be "sensorized" (i.e., have sensors) in order to know its position with respect one of the ends of platform 20. Second carriage 48 could also be motorized in order to be positioned electronically along direction 45. In this case there will be two positioning axes (the translation along direction 45 and the rotation about pivot 41) plus six axes for the robot for a total of eight axes.

Robotic arm assembly 40, which may be a six-axis robot, may perform the surgical procedure itself. The robotic arm assembly may include a sensorized guide, which may be used as a surgical instrument holder that is placed automatically in the right locations using the proper orientation. The surgical instrument may be inserted directly into the patient or into a cannula attached to the robotic arm assembly or sensorized guide at a single access point. The surgical procedure may be monitored using CT or fluoroscopy. Examples of robotic arm assemblies have been described in the following documents that are subject to an assignment to the applicant of this application or to an affiliate of the applicant: (1) U.S. Pat. App. Ser. No. 62/572,986, "Robot Assisted Surgical Guide System for Performing Surgery," filed Oct. 16, 2017; (2) U.S. Pat. App. Ser. No. 62/627,565, "Apparatus and Method for Controlling the Use of Surgical Instruments During Surgery," filed Feb. 7, 2018; (3) U.S. patent application Ser. No. 16/160,575, "Robot-Assisted Surgical Guide System for Performing Surgery," filed Oct. 15, 2018; (4) U.S. Pat. App. Ser. No. 62/630,612, "Method for Determination of Surgical Procedure Access," filed Feb. 14, 2018, and (5) U.S. patent application Ser. No. 16/275,313, "Method for Determination of Surgical Procedure Access," filed Feb. 13, 2019. The entireties of U.S. patent application Ser. Nos. 62/572,986, 62/627,565, 16/160,575, 62/630,612, and 16/275,313 are incorporated herein by reference to the extent applicable.

Figure 1D:
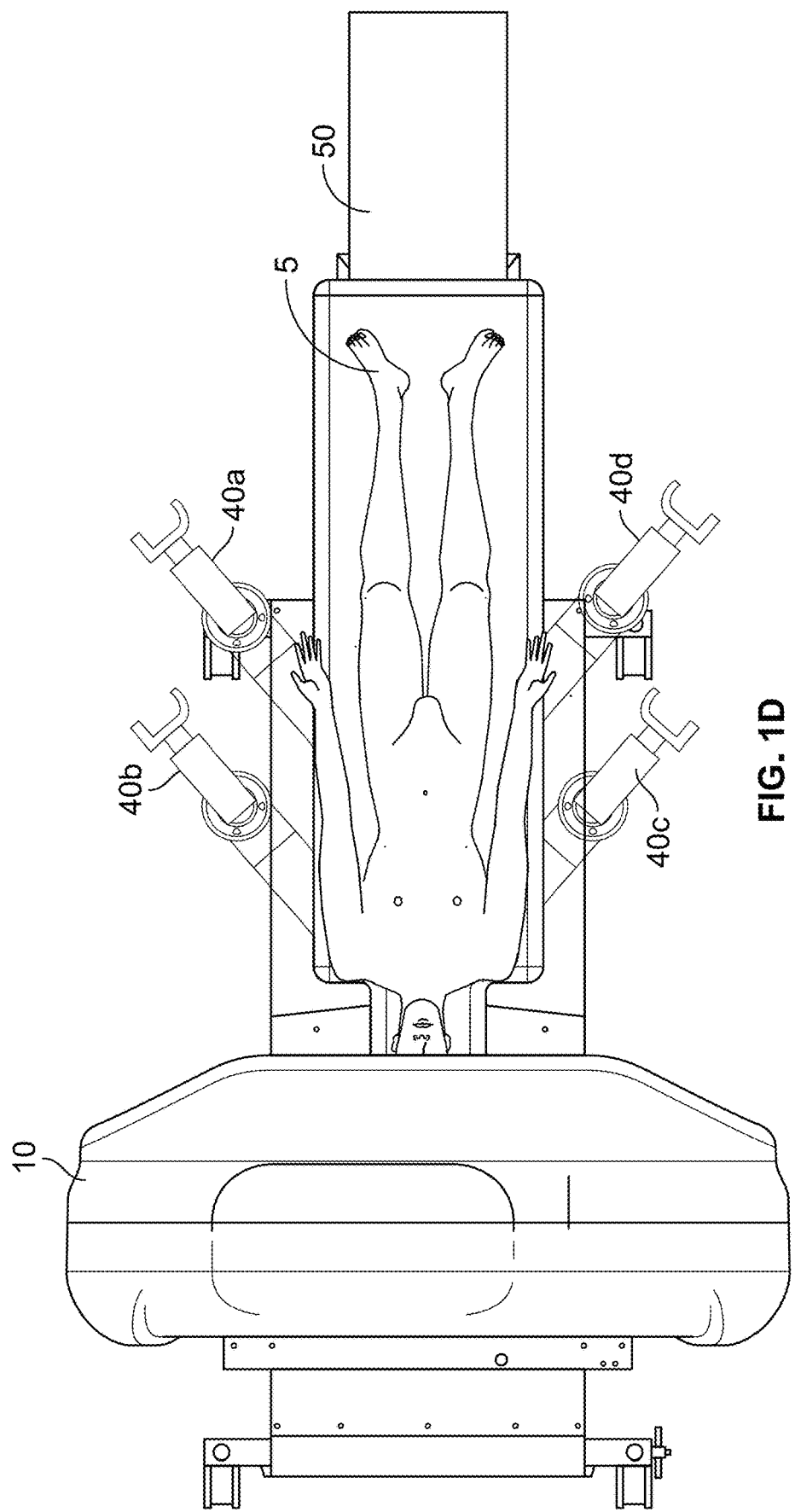
FIG. 1D is a top view of the system of FIG. 1A, showing four possible locations for the robotic arm assembly, according to embodiments of the present invention.

FIG. 1D is a top view of system 100, showing four possible locations for robotic arm assembly 40-40a, 40b, 40c, 40d. Locations 40a, 40d may be realized with second carriage 48 in the position shown in FIG. 1A; locations 40b, 40c may be realized with second carriage 48 in a second position, translated towards gantry 10 in direction 45. Location 40a may allow easier access to the patient's lower left side during surgery; location 40b may allow easier access to the patient's upper left side during surgery; location 40c may allow easier access to the patient's upper right side during surgery; and location 40d may allow easier access to the patient's lower right side during surgery.

The operation of system 100, and other systems described in this specification, are generally consistent with the operation of systems described in the following documents that are subject to an assignment to the applicant of this application or to an affiliate of the applicant: (1) PCT International Publication No. WO 2017/134546, "Radiological Imaging Device," published Aug. 10, 2017; (2) U.S. Pat. Pub. No. 2019/038240, "Radiological Imaging Device," published Feb. 7, 2019; (3) U.S. Pat. No. 9,510,793, "Radiological Imaging Device with Advanced Sensors," issued Dec. 6, 2016; (4) U.S. Pat. No. 10,016,171, "Radiological imaging device with improved functionality," issued Jul. 10, 2018; and (5) U.S. Pat. No. 10,265,042, "Radiological imaging device with improved functioning," issued Apr. 23, 2019. The entireties of WO 2017/134546, U.S. Pat. Pub. No. 2019/038240, and U.S. Pat. Nos. 9,510,793, 10,016,171, and 10,265,042 are incorporated herein by reference to the extent applicable.

Figure 2A:
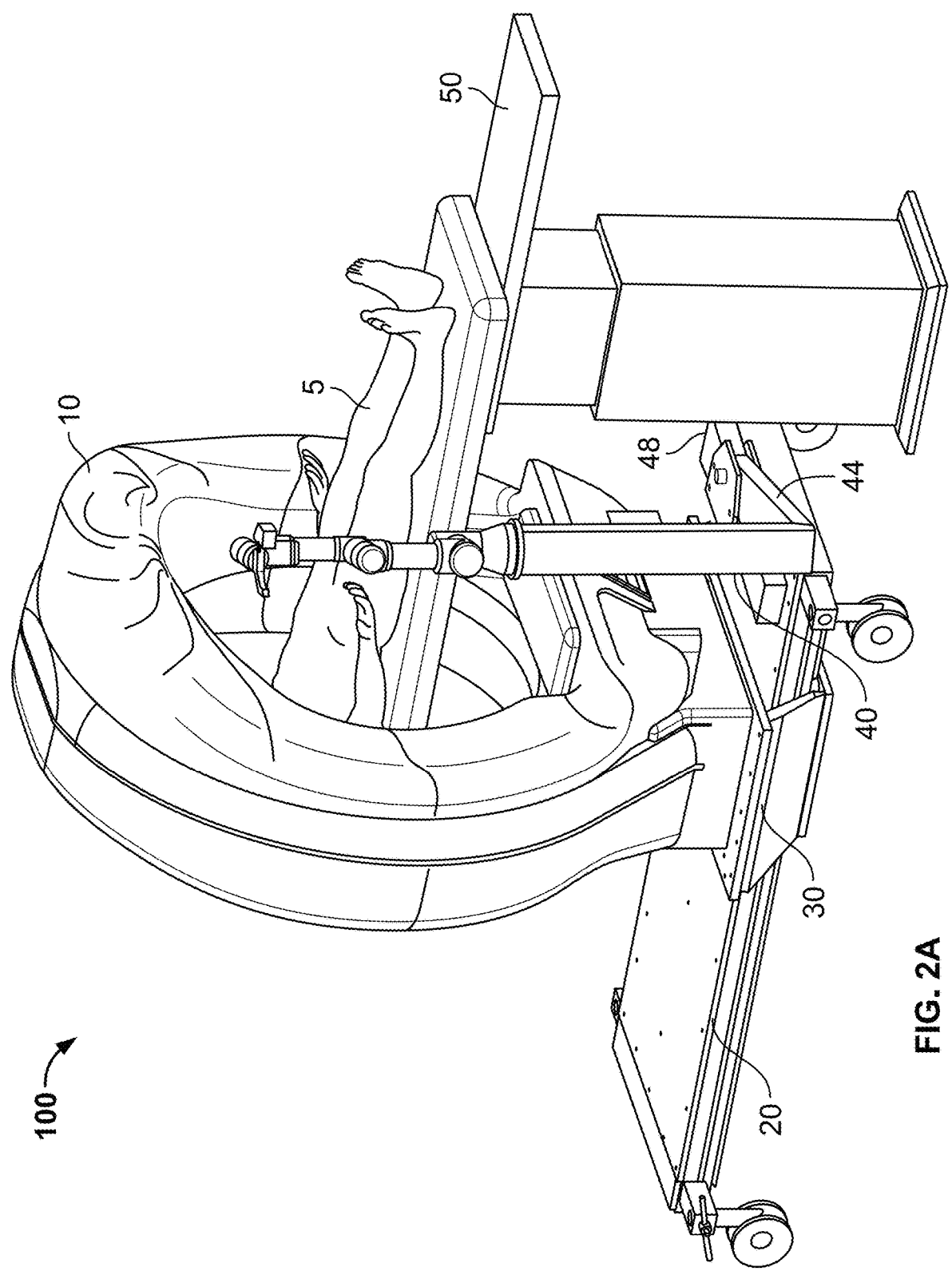
FIGS. 2A and 2B show uses of the system of FIG. 1A during abdominal cavity operations, according to embodiments of the invention.
Figure 2B:
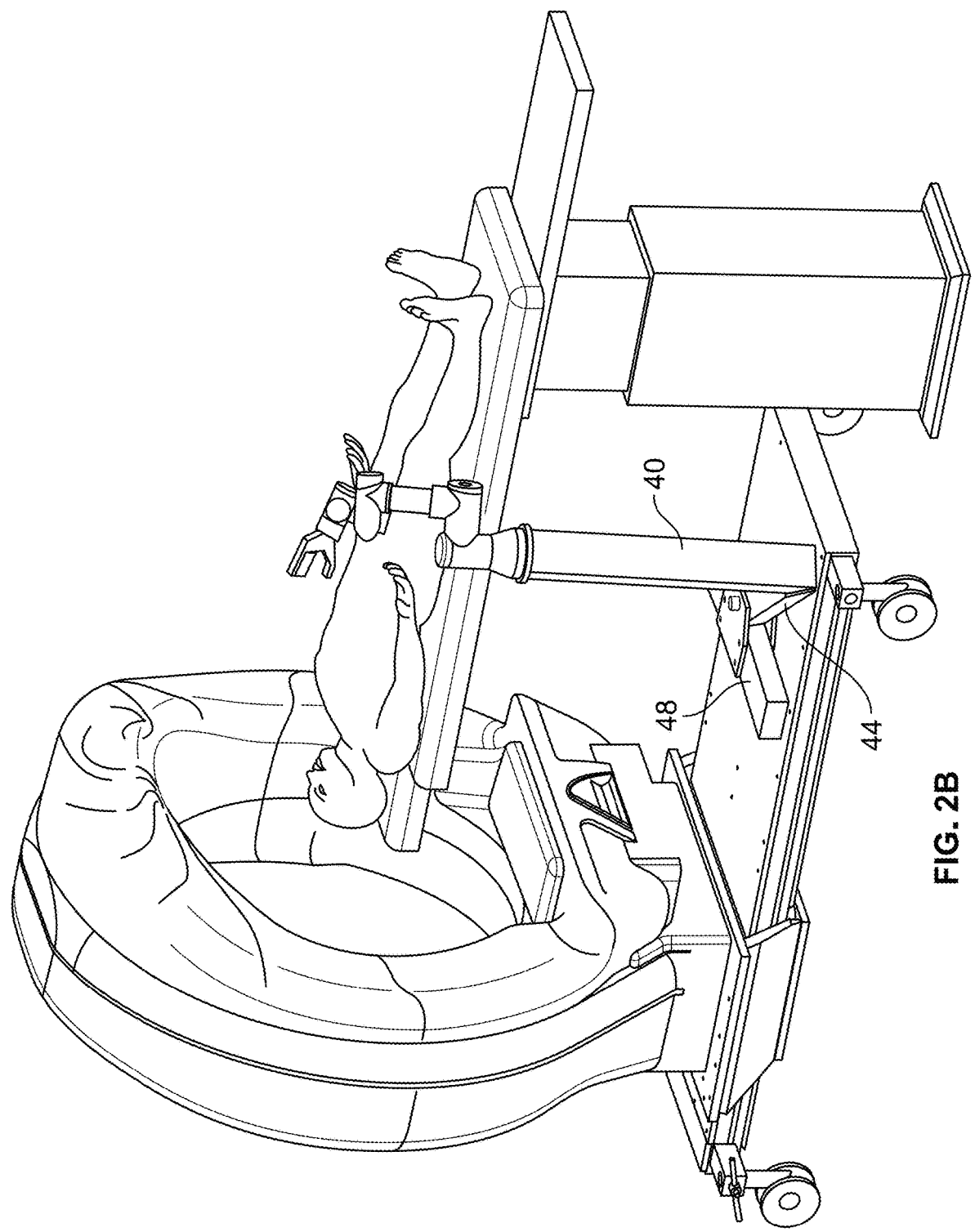

FIGS. 2A and 2B show uses of system 100 during abdominal cavity operations, according to embodiments of the invention. In FIG. 2A, gantry 10 may move forward on platform 20 in order to perform a scan or a fluoroscopy, either prior to or during surgery. In FIG. 2B, after the scan, gantry 10 may move back, and robotic arm assembly 40 may move via movement of second carriage 48 and pivot arm 44 so that the robot may perform (or assist in) surgery.

Figure 3B:
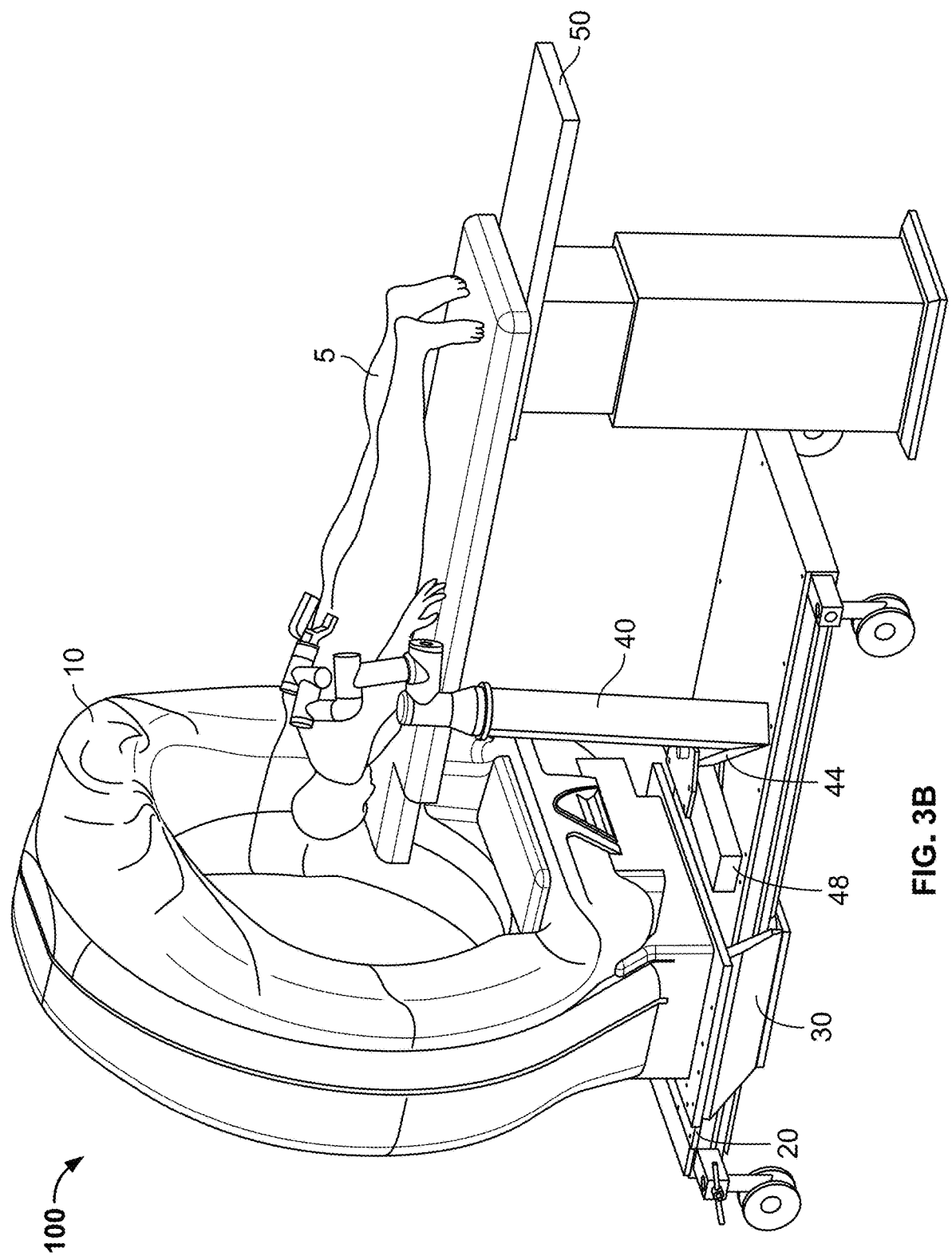
Figure 3C:
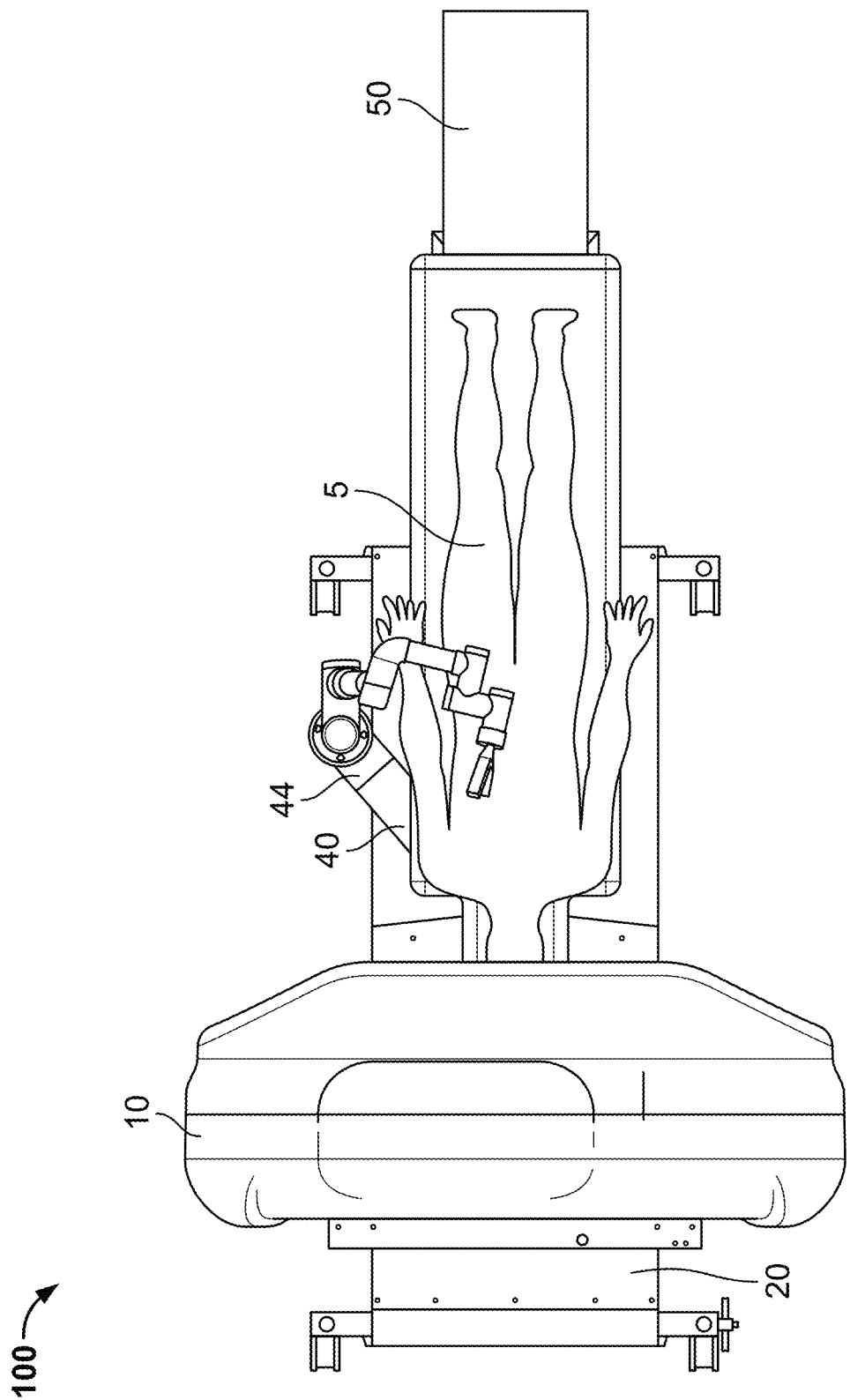

FIGS. 3A-3C show uses of system 100 during thoracic operations (on the patient's spine), according to embodiments of the invention. In FIG. 3A, gantry 10 may move forward on platform 20 in order to perform a scan or a fluoroscopy, either prior to or during surgery. In FIG. 3B, after the scan, gantry 10 may move back, and robotic arm assembly 40 may move via movement of second carriage 48 and pivot arm 44 so that the robot may perform (or assist in) surgery. FIG. 3C shows a top view of FIG. 3B in which robotic arm assembly 40 has pivoted to the other side of bed 50 to perform an operation from the right side of the patient.

Figure 4A:
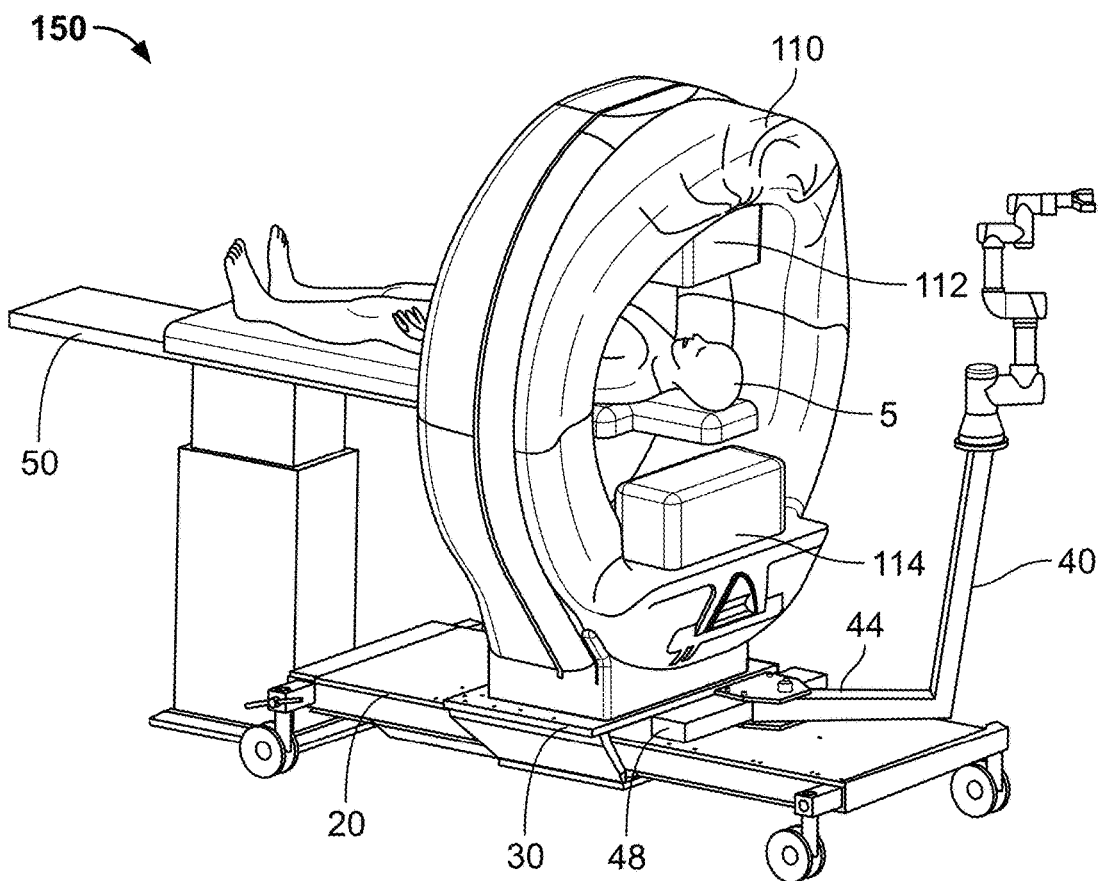
FIGS. 4A-4C show uses of another system for performing robotic surgery, according to embodiments of the invention.
Figure 4B:
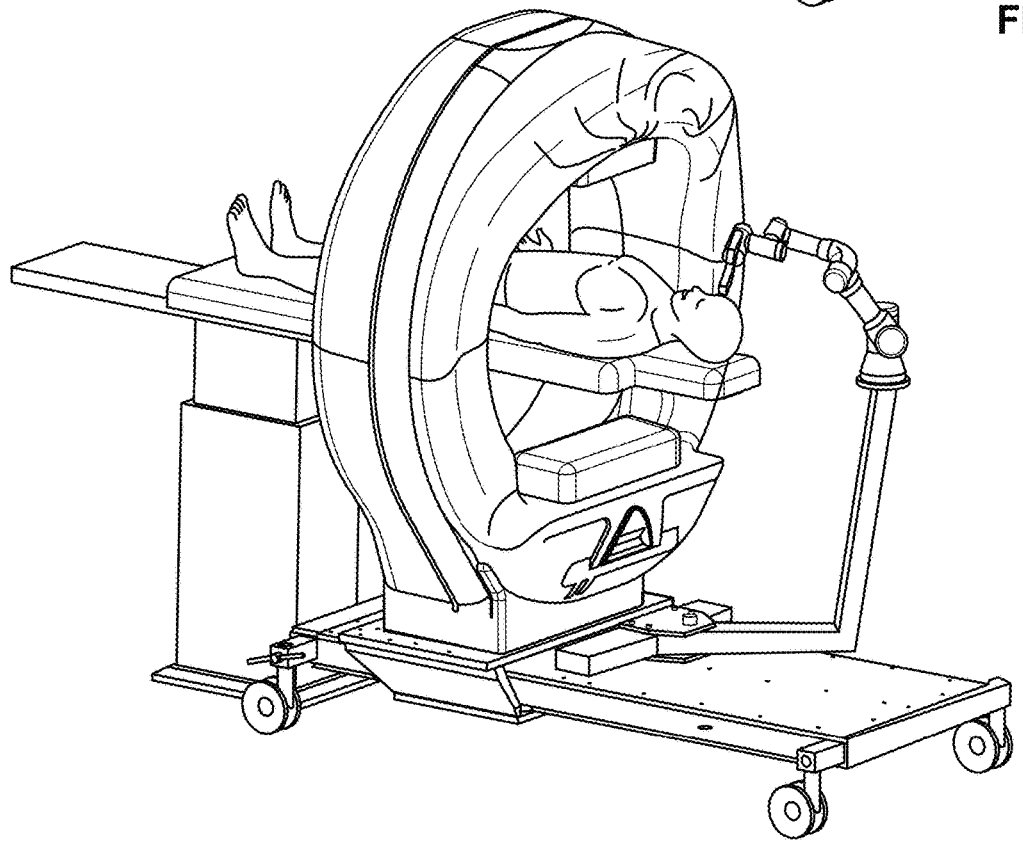
Figure 4C:
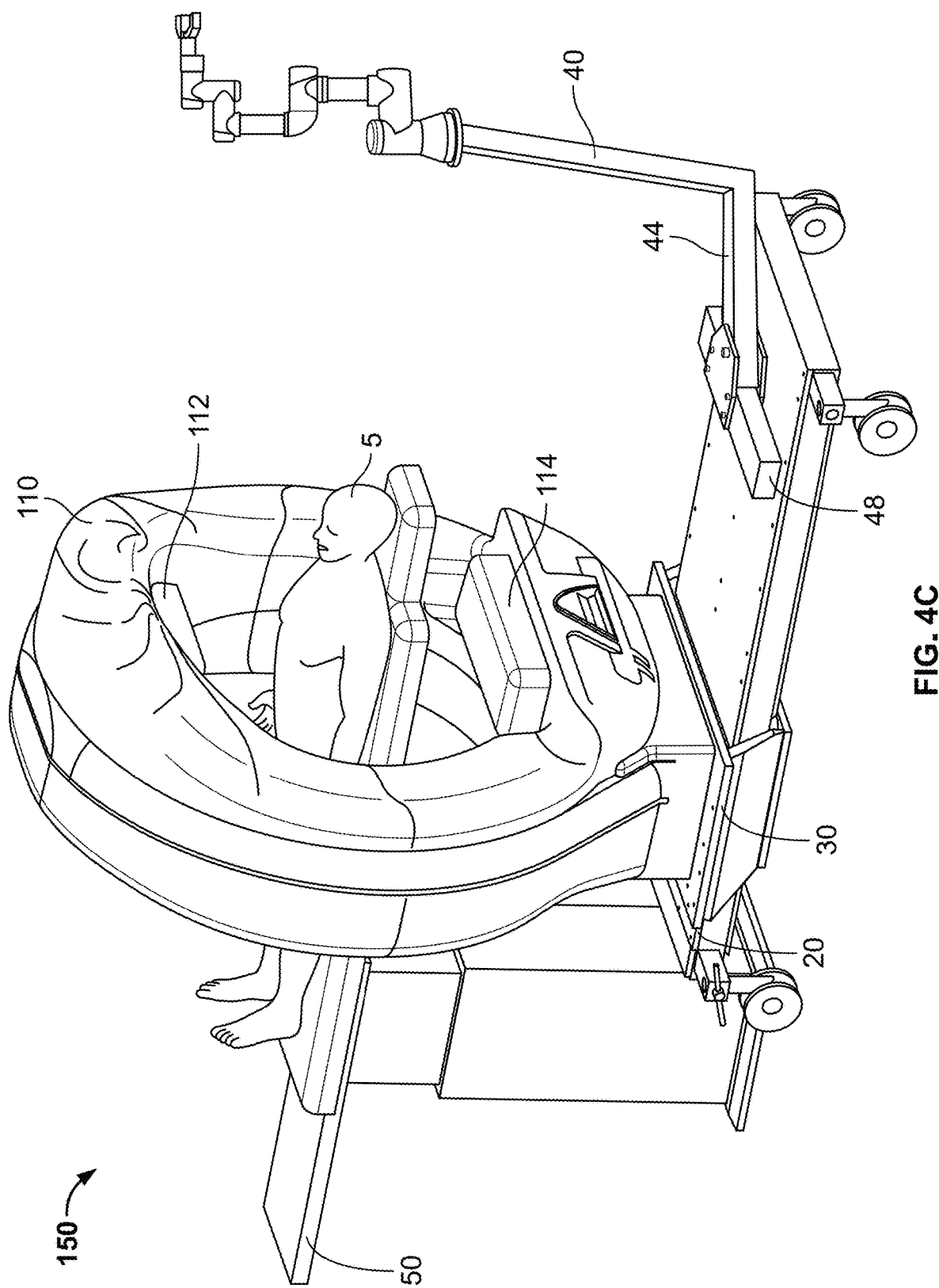

FIGS. 4A-4C show uses of a system 150 during brain operations, according to embodiments of the invention. System 150 is a modified version of system 100, in which gantry 110 includes x-ray source 112 and x-ray detector 114, which are movable toward and away from each other. Having the source and detector movable increases the scan resolution, which is important for brain surgery. In FIGS. 4A-4C, patient 5 and bed 50 approach system 150 from the opposite direction illustrated in previous figures.

In FIG. 4A, gantry 110 may move forward on platform 20 in order to perform a scan or a fluoroscopy, either prior to or during surgery. In FIG. 4B, after the scan, gantry 110 may move back, x-ray source 112 and x-ray detector 114 may retract, and robotic arm assembly 40 may move via movement of second carriage 48 and pivot arm 44 so that the robot may perform (or assist in) surgery. FIG. 4C shows that robotic arm assembly 40, via movement of second carriage 48 and pivot arm 44, may move out of the operating area if desired.

Figure 5A:
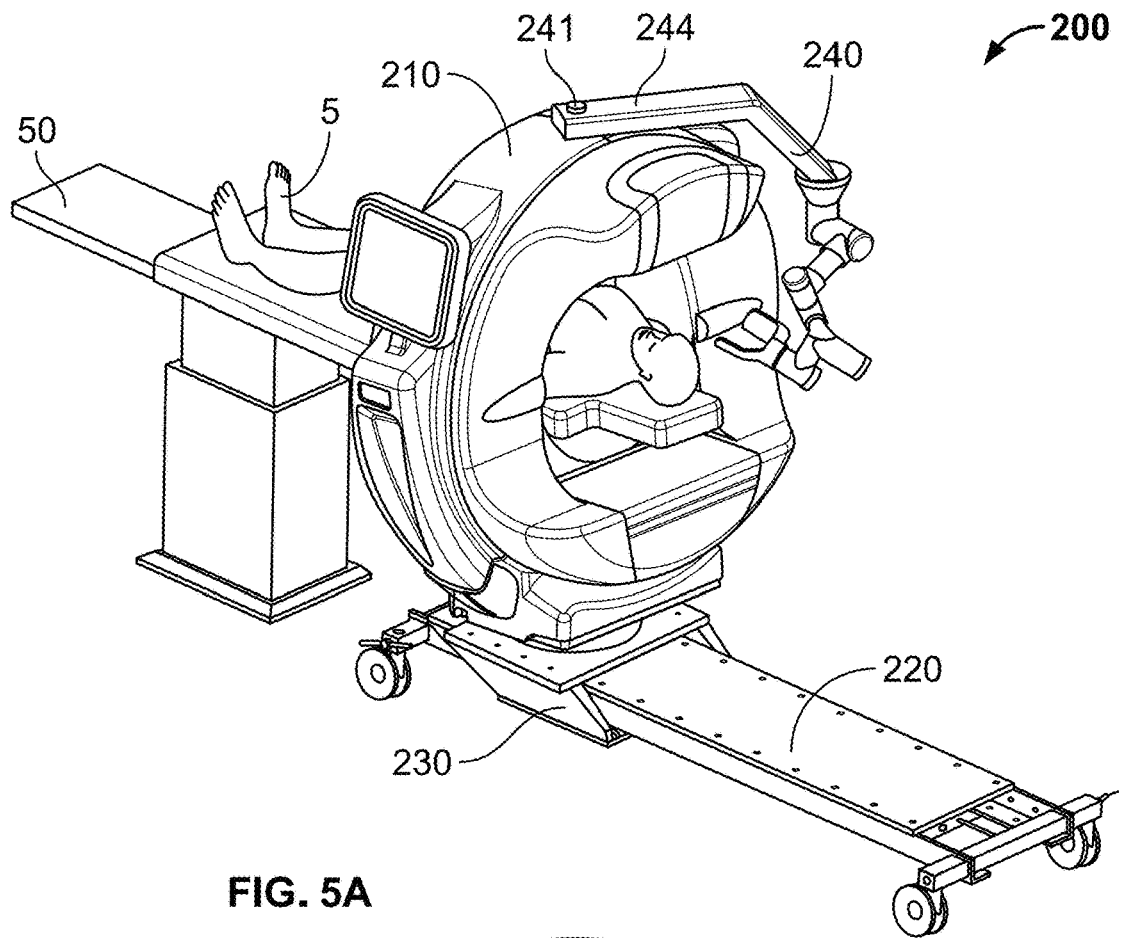
FIGS. 5A-5B are diagrams of another system for performing robotic surgery, according to embodiments of the present invention.

FIG. 5A shows a system 200 for performing robotic surgery, according to an embodiment of the present invention. System 200 varies from systems 100 and 150 in a few ways. First, the bore diameter of gantry 210 is generally smaller than that of gantries 10 and 110—on the order of 60 cm rather than 95 cm or more. Such gantries are more suited for brain operations, and possibly for pediatric and veterinary operations. Gantry 210 also contains within it a CT scanning and imaging device, is supported by platform 220, and may move via carriage 230 in order to engage and disengage the CT with patient 5 disposed on bed 50. Platform 220 may have wheels as did platform 20. An example of a CT device to be used within system 200 is Epica International's Vimago™ CT scanner.

Second, system 200 includes robotic arm assembly 240, which may be attached via pivot arm 244 to pivot 241 at the top center of gantry 210. Pivot 241 and pivot arm 244 may operate in the same manner as pivot 41 and pivot arm 44 in system 100. Pivot 241 may also be replaced by a motor shaft and a motor and control system as described with respect to system 100. In these ways, robotic arm assembly 240 may operate on either side of gantry 210, and may operate on the right or left side of the patient's body.

Figure 5B:
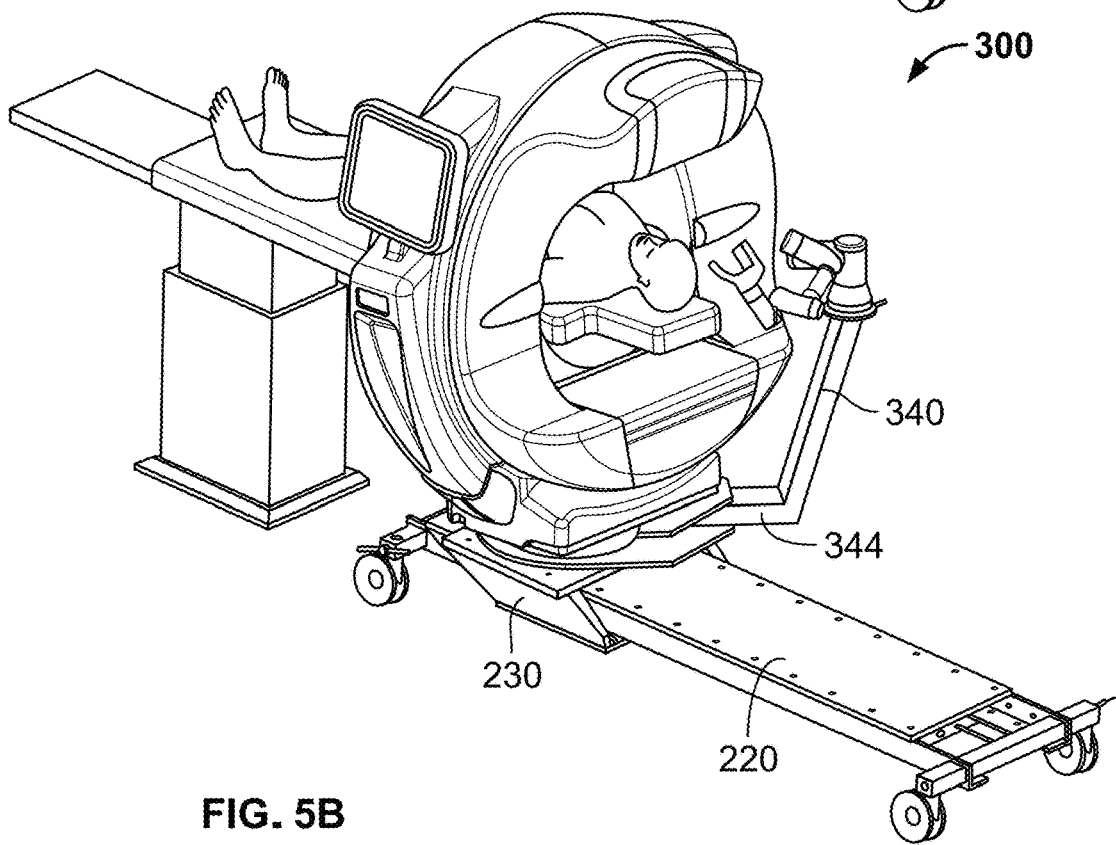

FIG. 5B shows a system 300 for performing robotic surgery, according to an embodiment of the present invention. System 300 varies from system 200 in that robotic arm assembly 340 is attached via pivot arm 344 at the bottom center of gantry 210. Except for the placement of the pivot, robotic arm assembly 340 operates in the same manner as robotic arm assembly 240. In addition, any of the drawings that follow that show the robotic arm assembly being attached at the top of the gantry may be modified by having the robotic arm assembly attached to the bottom of the gantry, as shown in FIG. 5B.

Figure 6A:
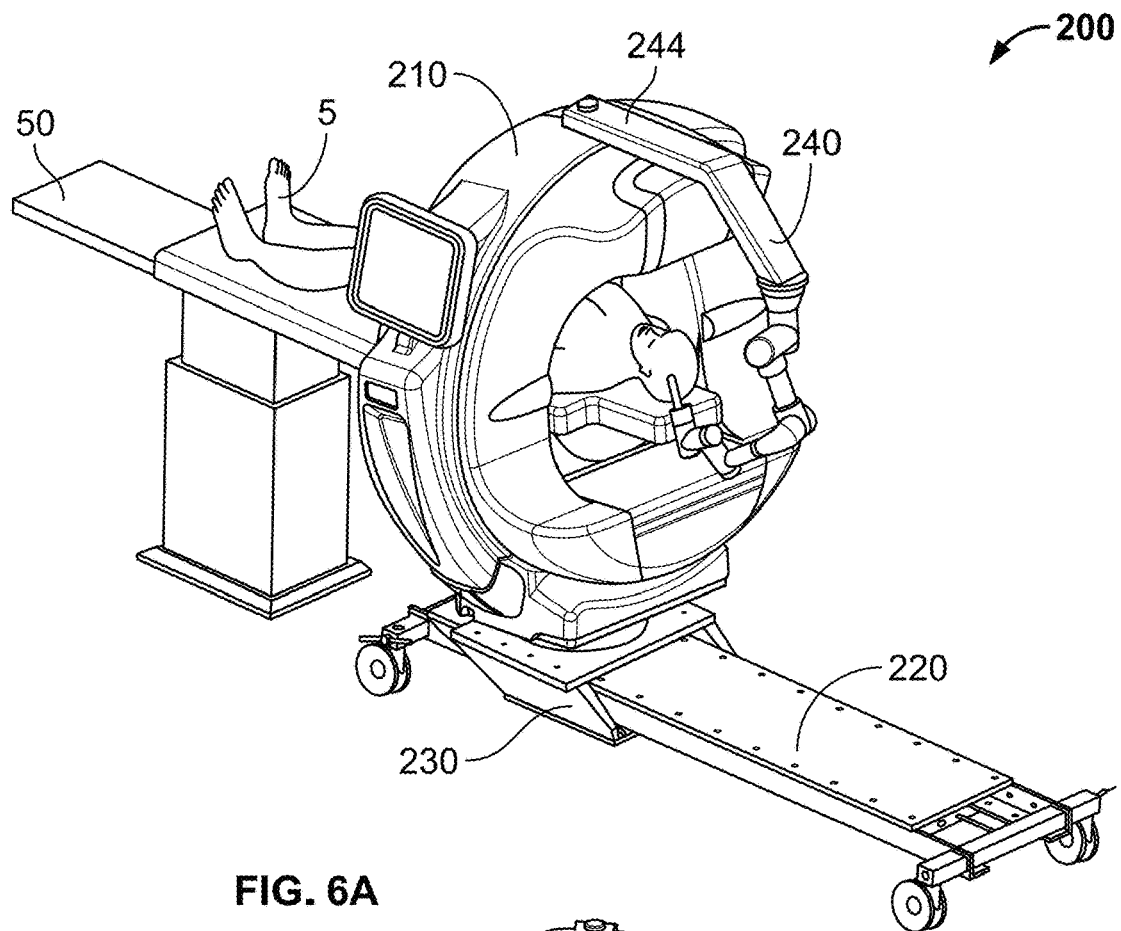
FIGS. 6A-6D show uses of the systems of FIGS. 5A-5B during robotic surgery, according to embodiments of the invention.
Figure 6B:
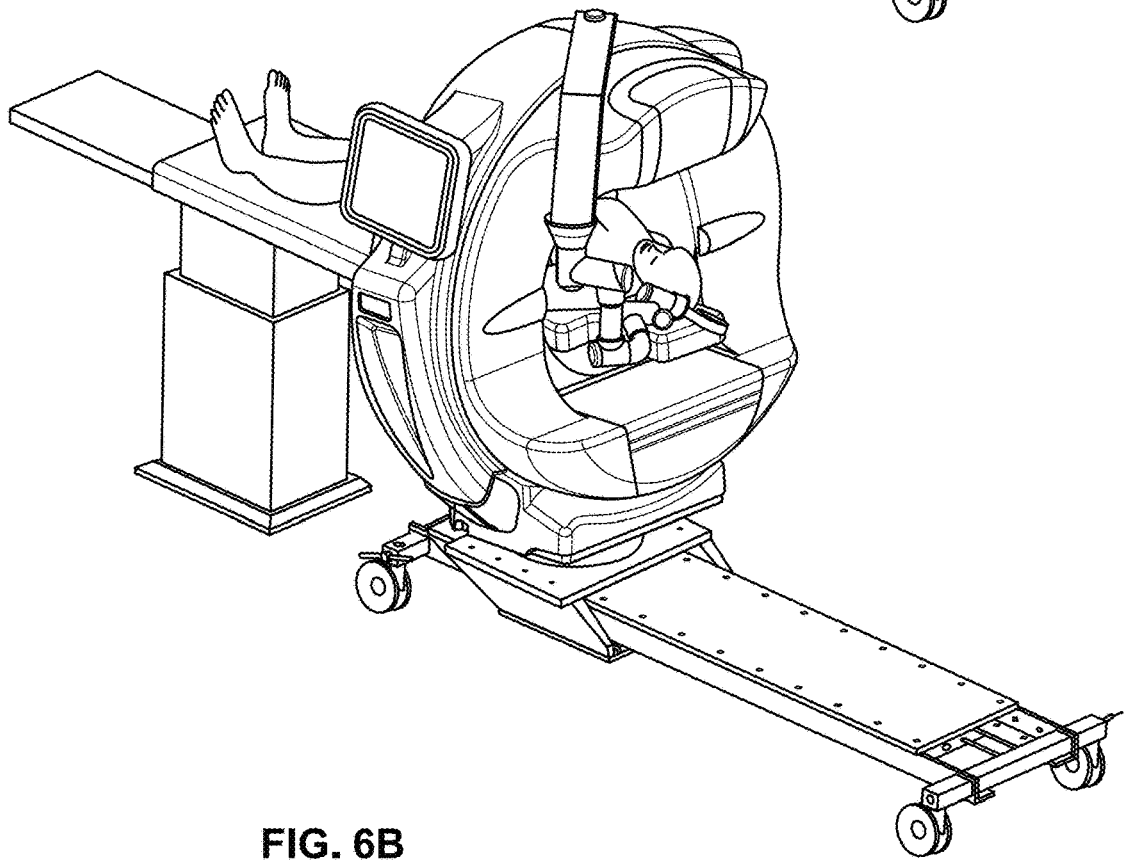
Figure 6C:
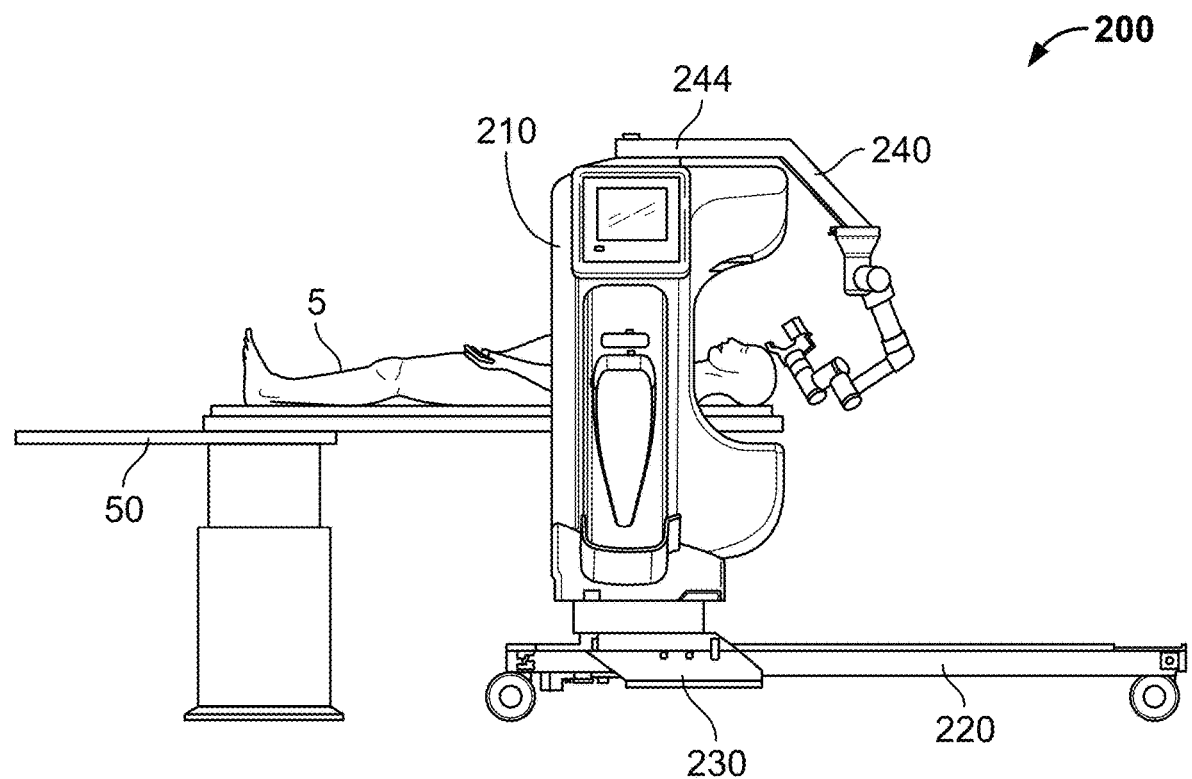
Figure 6D:
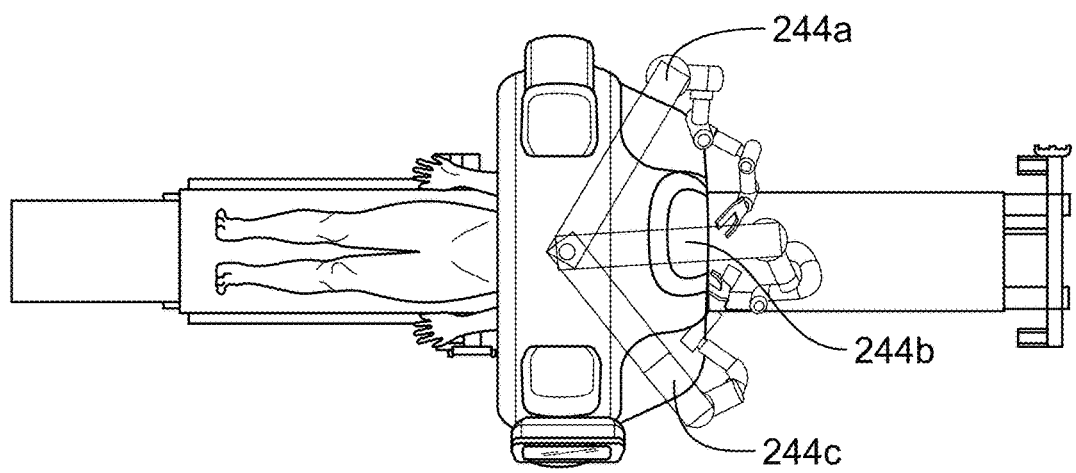

FIGS. 6A-6D show uses of system 200 (and 300) during operations with robotic arm assembly 240 and pivot arm 244 disposed on the front side of gantry 210, according to embodiments of the invention. In these embodiments, the patient's area of interest (e.g., brain) may be within the CT analysis zone of gantry 210. FIG. 6A shows robotic arm assembly 240 and pivot arm 244 in the front center position, and FIG. 6B shows robotic arm assembly 240 and pivot arm 244 in the front right position. FIG. 6C shows a side view of an operation with robotic arm assembly 240 and pivot arm 244 on the front side of gantry 210. FIG. 6D shows a top view of three different positions for robotic arm assembly 240 and pivot arm 244—location 244a, front left; location 244b, front center; and location 244c, front right. There may be more than three positions on the front side of gantry 210 into which robotic arm assembly 240 may be placed, the mechanics of which were described with respect to FIGS. 1B and 1C.

Figure 7A:
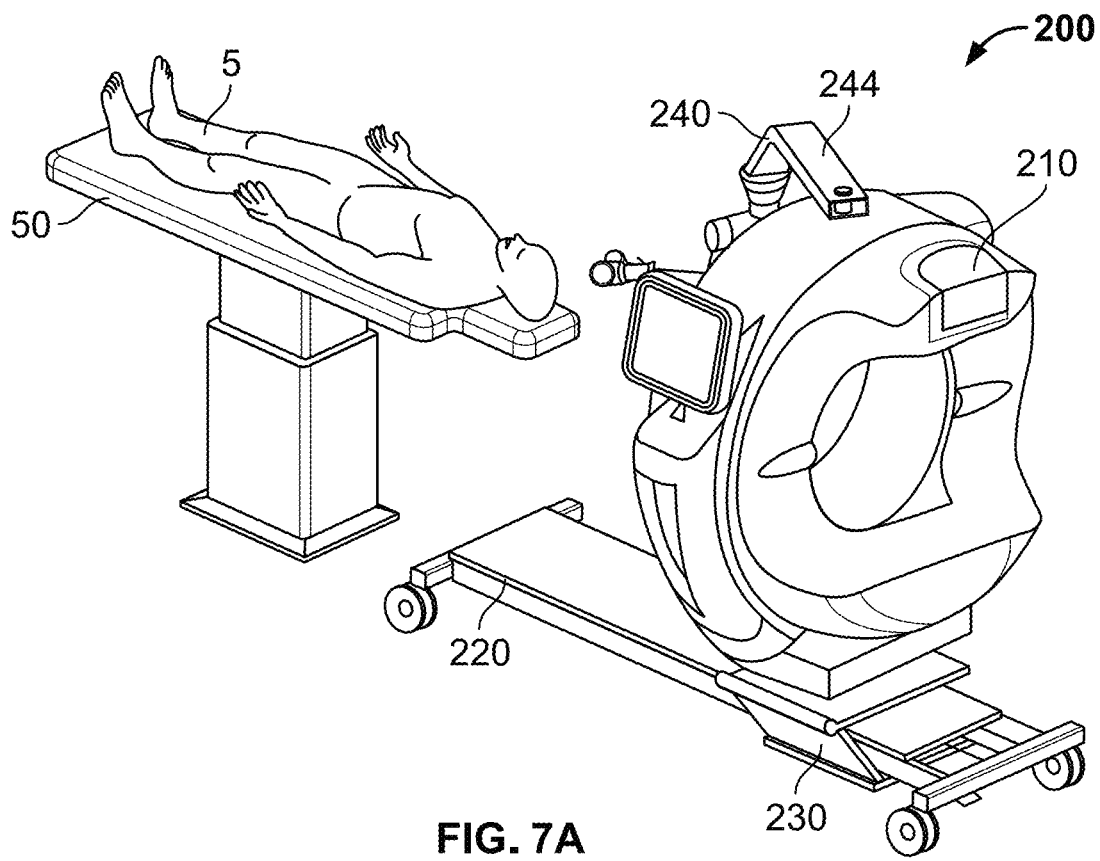
FIGS. 7A-7C show additional uses of the systems of FIGS. 5A-5B during robotic surgery, according to embodiments of the invention.
Figure 7B:
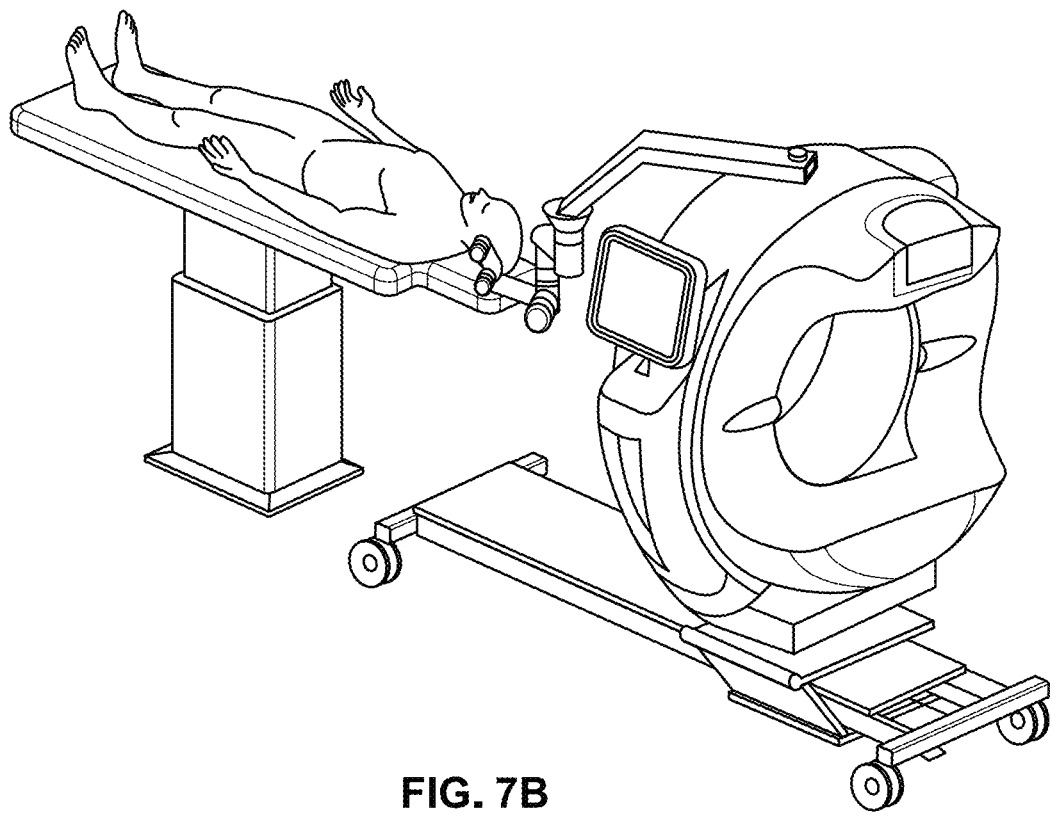
Figure 7C:
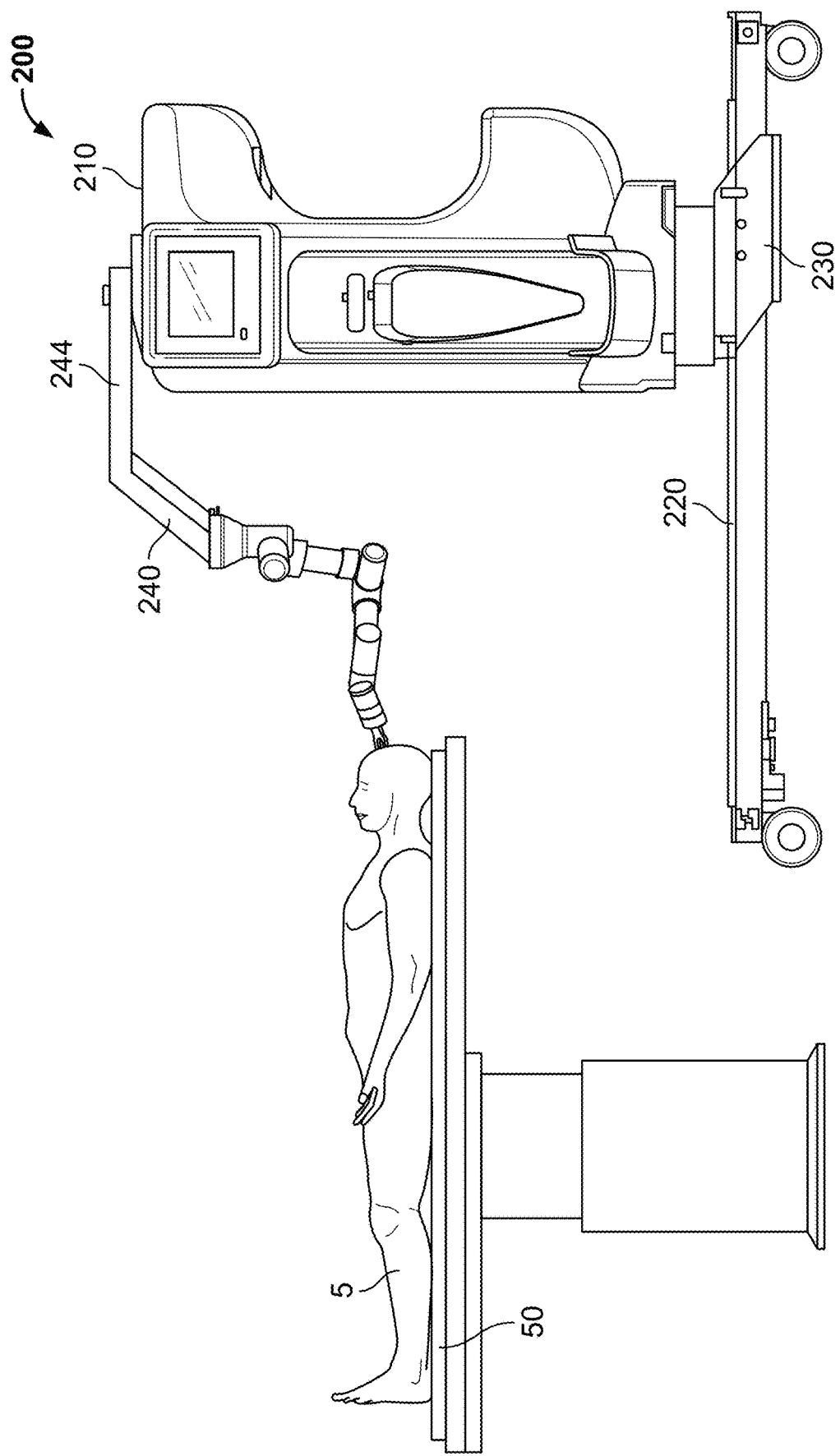

FIGS. 7A-7C show uses of system 200 (and 300) during operations with robotic arm assembly 240 and pivot arm 244 disposed on the back side of gantry 210, according to embodiments of the invention. In those examples, gantry 210 may move forward on platform 220 out of the way of the patient. FIG. 7A shows robotic arm assembly 240 and pivot arm 244 in the back left position, and FIG. 7B shows robotic arm assembly 240 and pivot arm 244 in the back right position. FIG. 7C shows a side view of an operation with robotic arm assembly 240 and pivot arm 244 on the back side of gantry 210. Robotic arm assembly 240 may be placed in more than these positions on the back side of gantry 210, the mechanics of which were described with respect to FIGS. 1B and 1C.

Figure 8A:
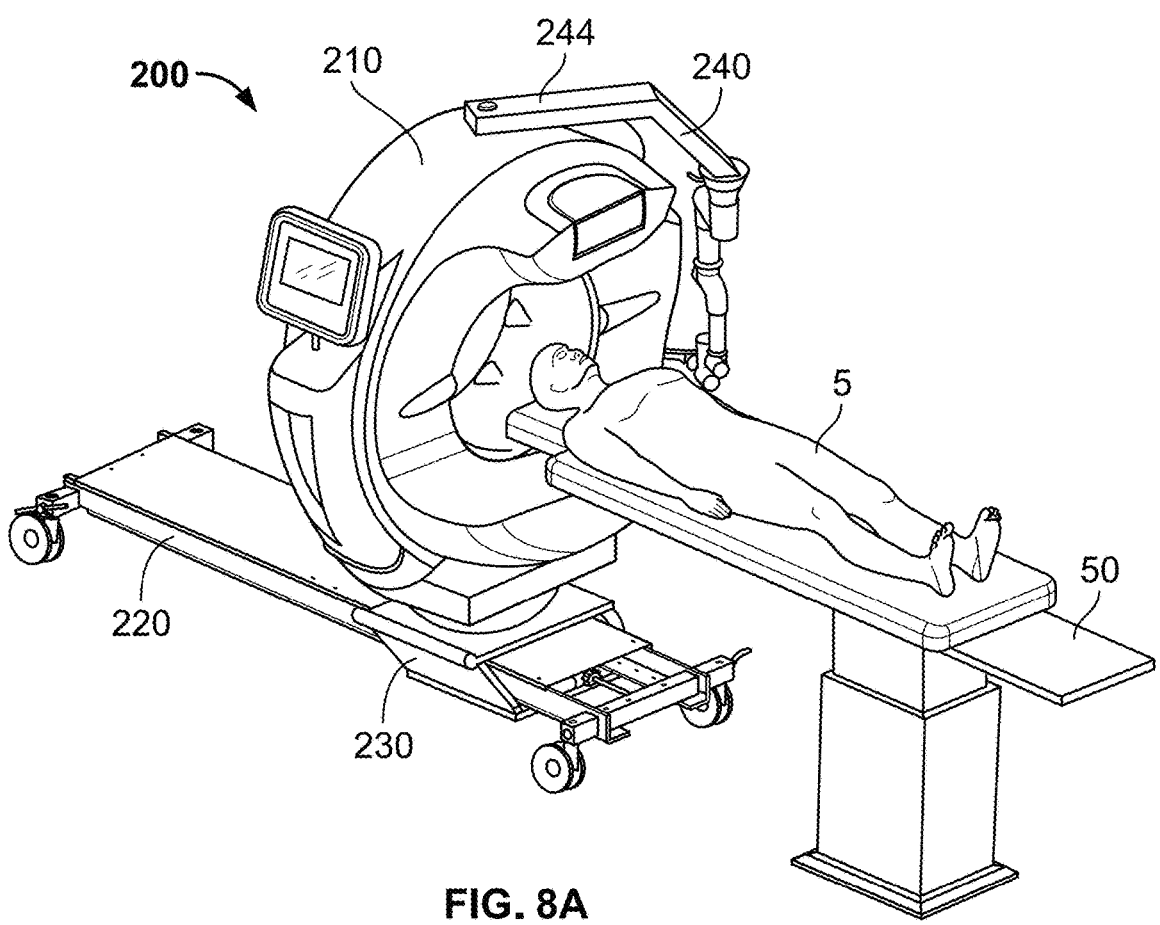
FIGS. 8A-8D show additional uses of the systems of FIGS. 5A-5B during robotic surgery, according to embodiments of the invention.
Figure 8B:
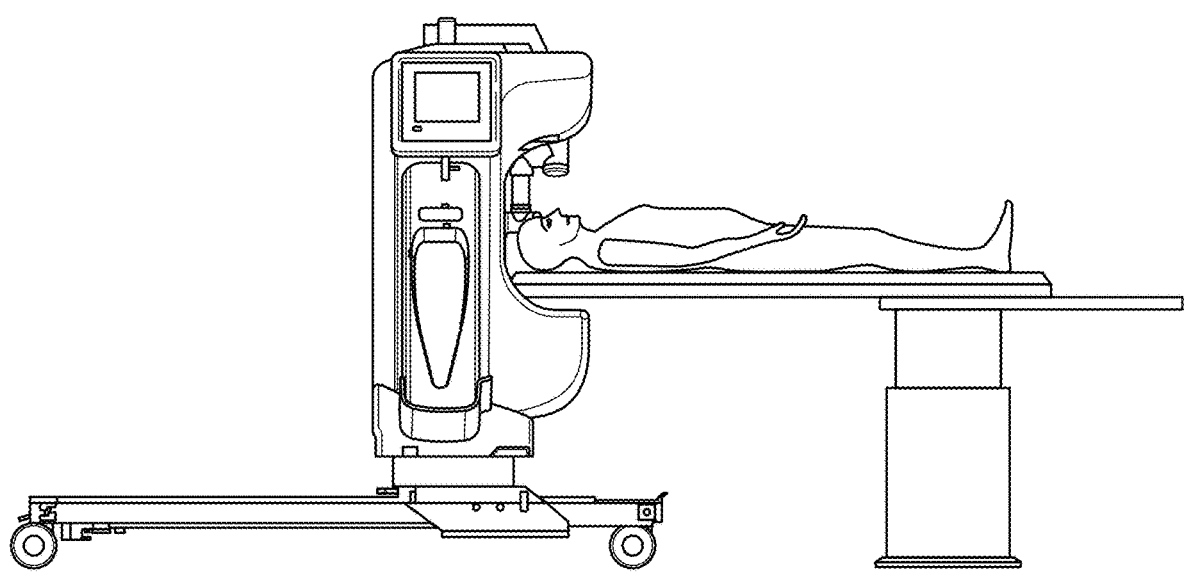
Figure 8C:
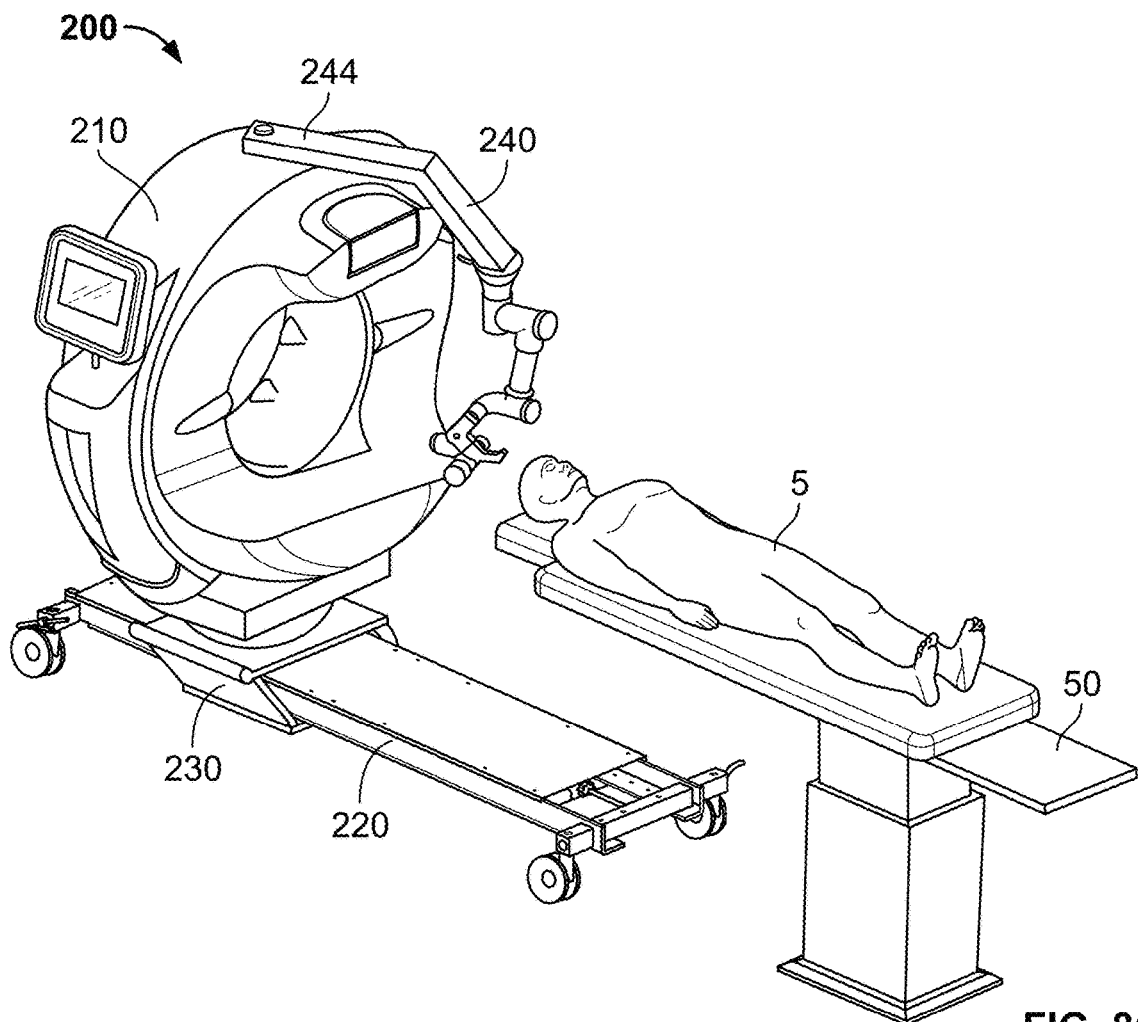
Figure 8D:
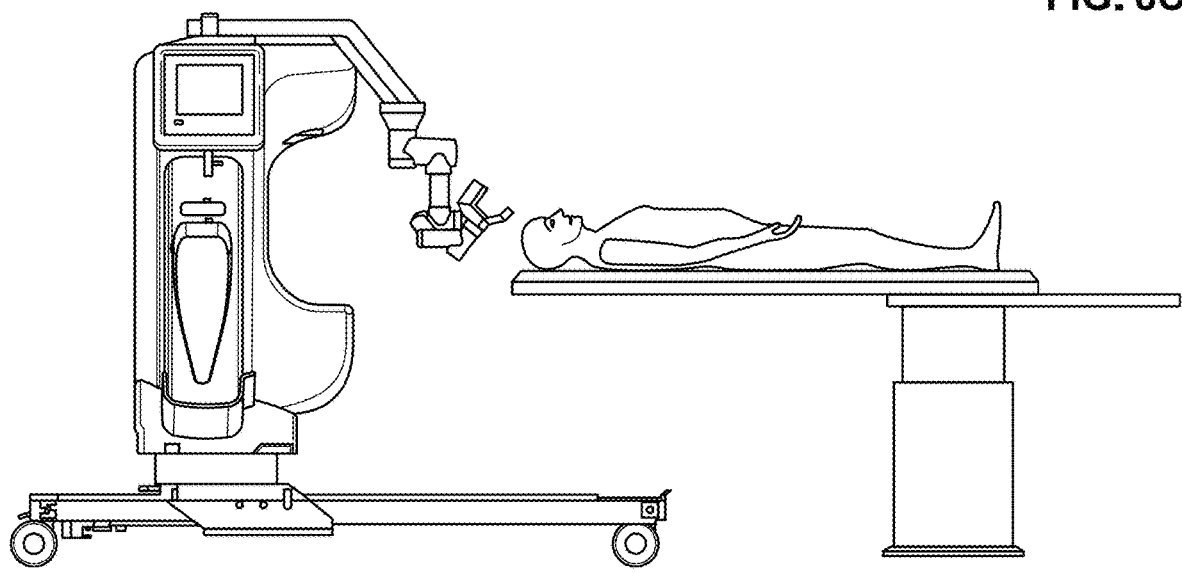

FIGS. 8A-8D show uses of system 200 (and 300) during operations with robotic arm assembly 240 and pivot arm 244 again disposed on the front side of gantry 210, according to embodiments of the invention. The patient and table are located on the front side of gantry 210 rather than on the back side, as was shown in FIGS. 6A-6D. In FIGS. 8A (perspective view) and 8B (side view), the patient's area of interest (e.g., brain) may be within the CT analysis zone of gantry 210 during the operation. In FIGS. 8C (perspective view) and 8D (side view), platform 220 and gantry 210 have been moved so that the patient is no longer within the CT analysis zone of gantry 210 during the operation.

Figure 9A:
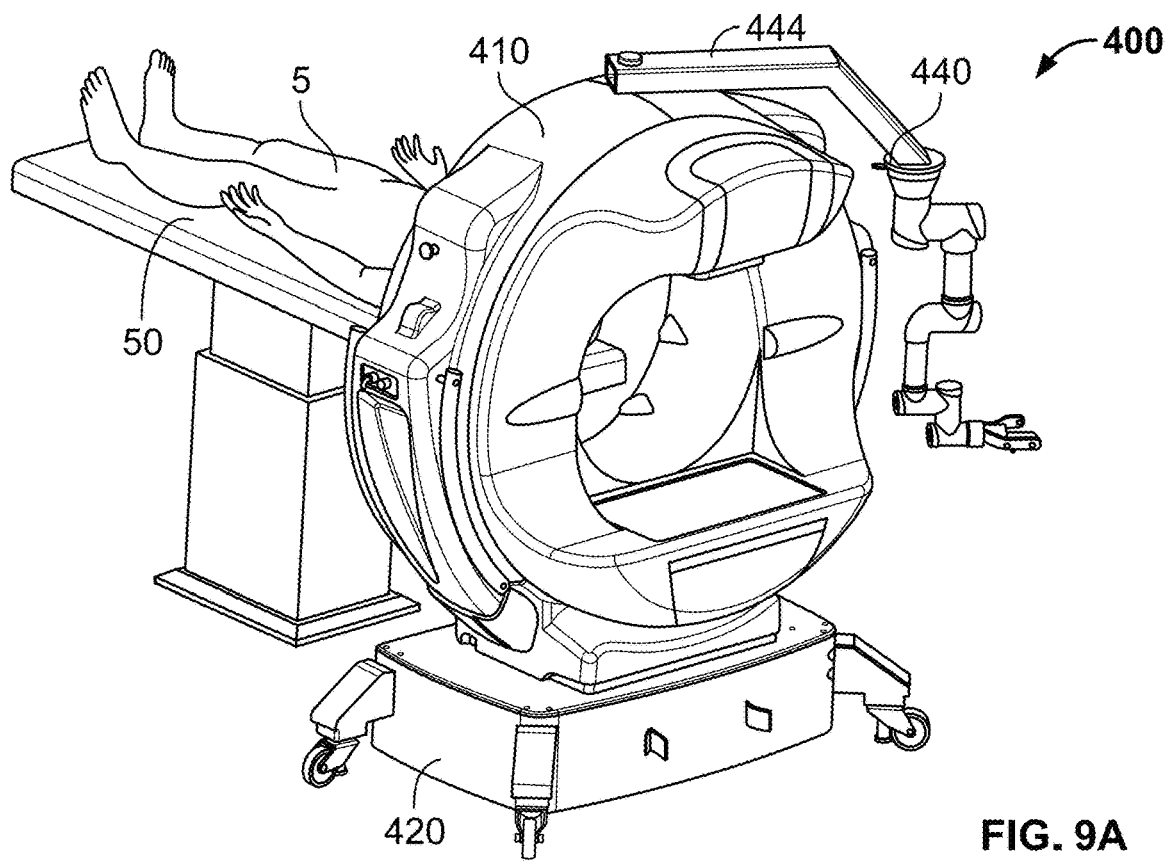
FIGS. 9A-9F are diagrams of another system for performing robotic surgery, according to embodiments of the present invention.
Figure 9B:
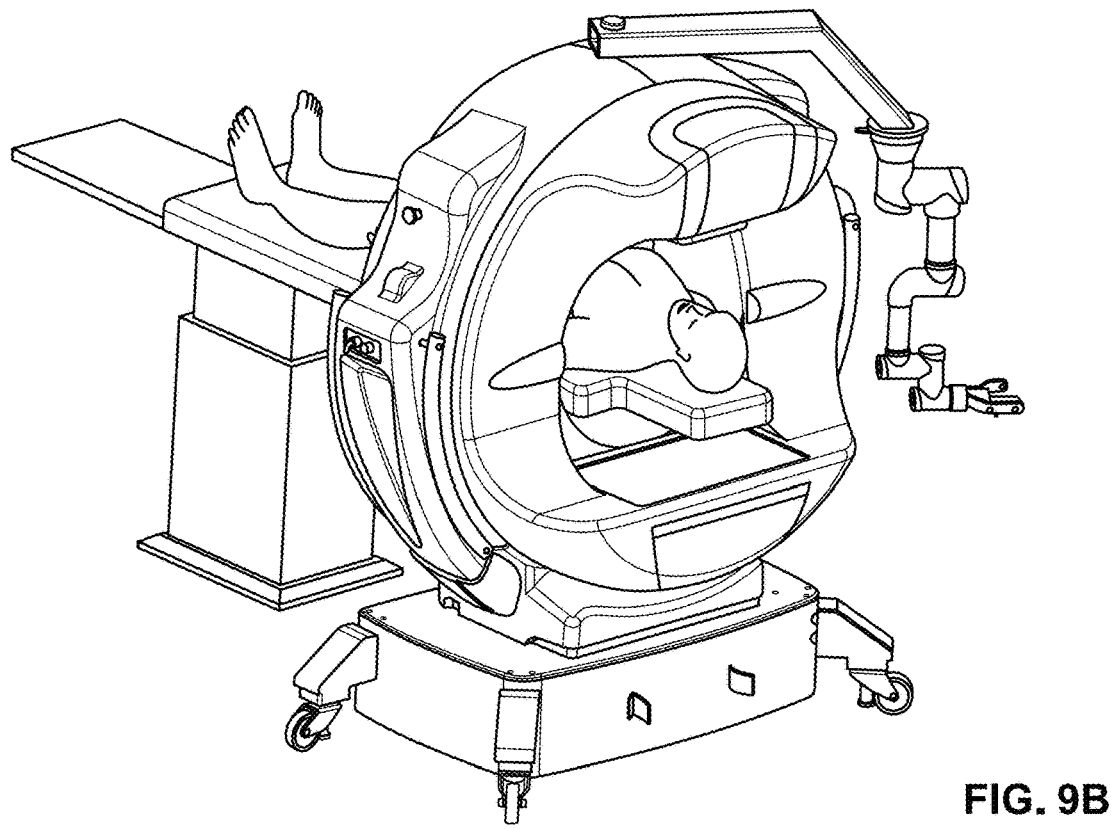
Figure 9C:
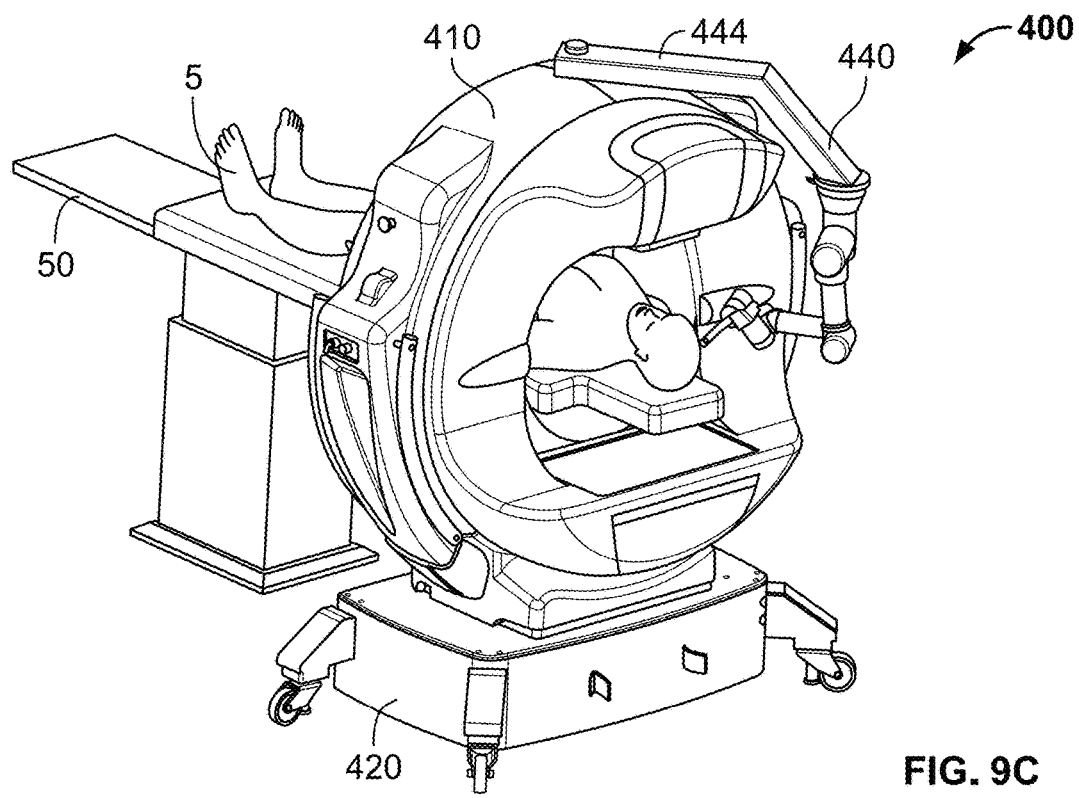
Figure 9D:
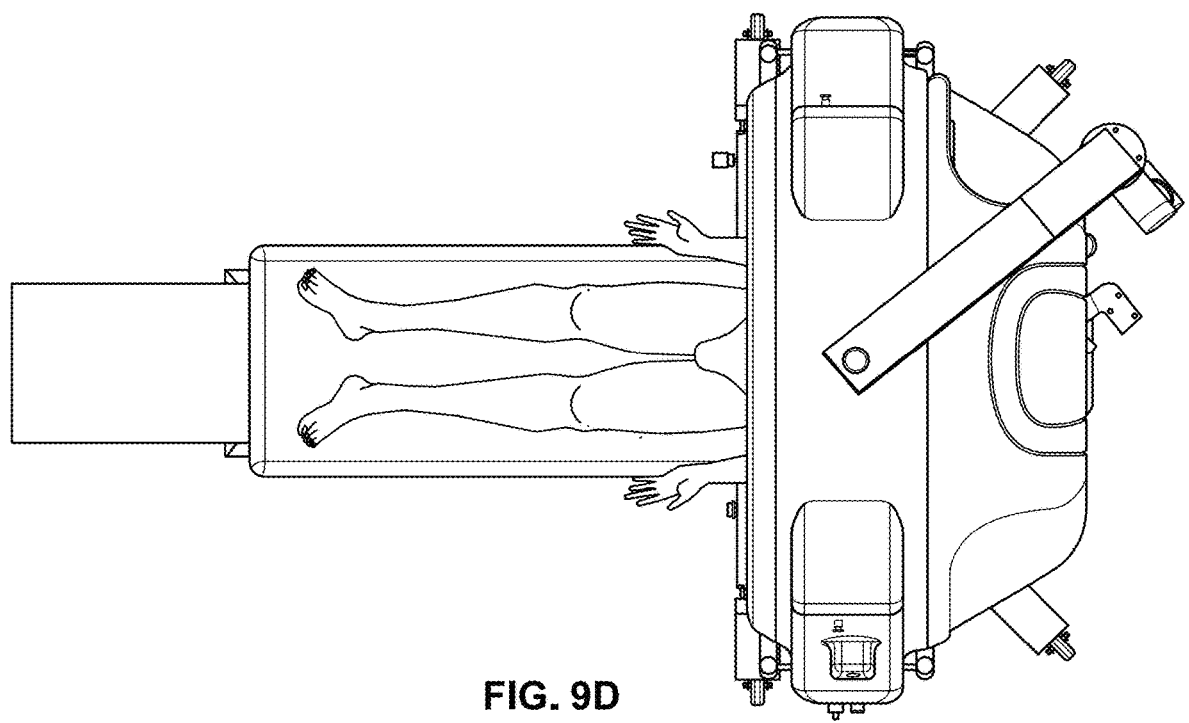
Figure 9E:
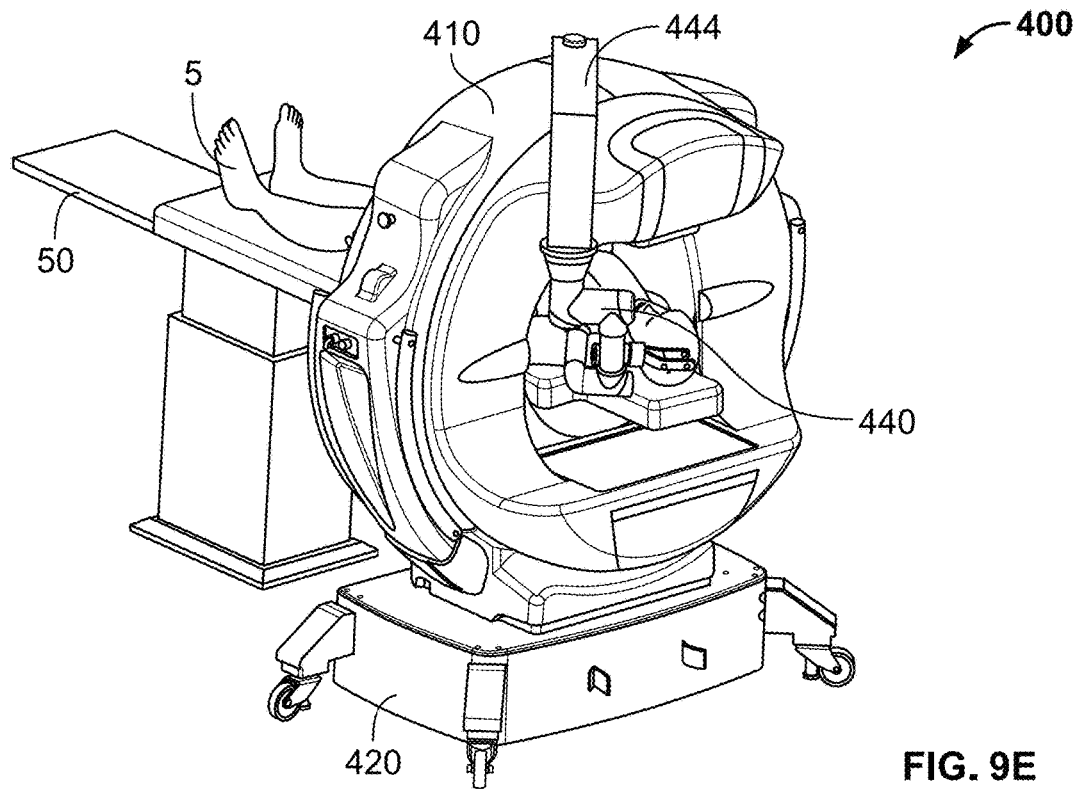
Figure 9F:
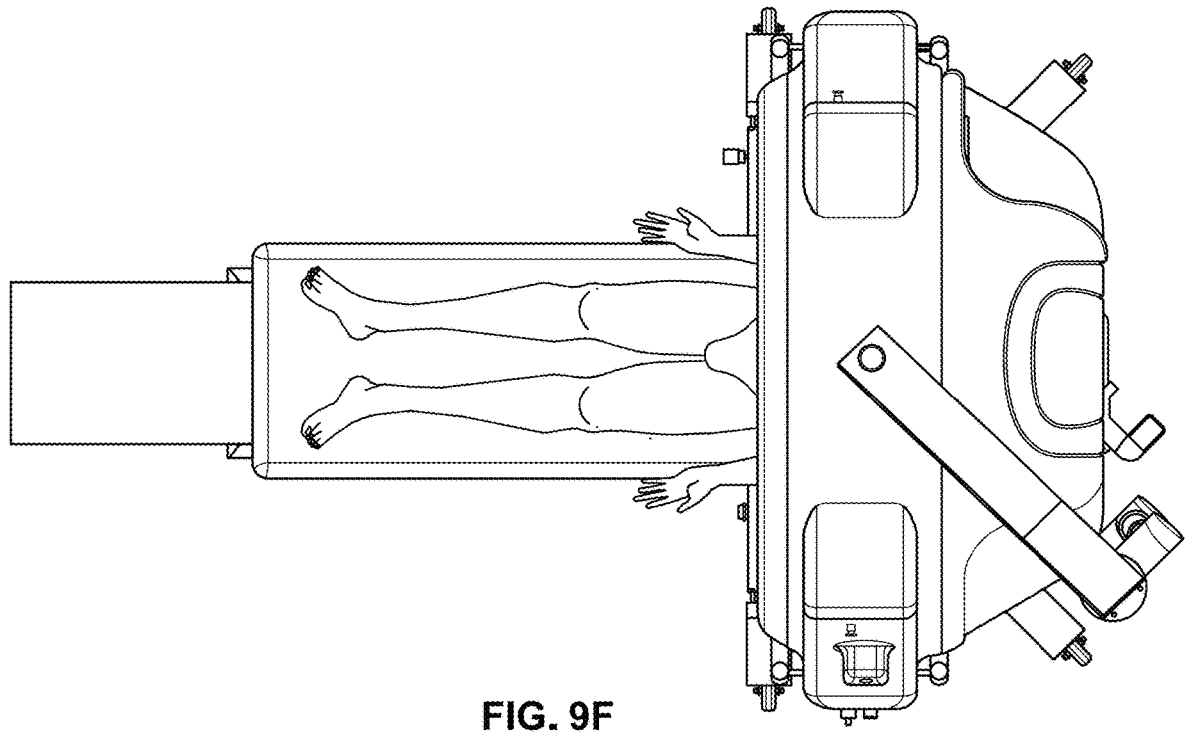

FIGS. 9A-9F show a system 400 for performing robotic surgery, according to an embodiment of the present invention. System 400 varies from systems 200 and 300 in that platform 420 is smaller, and there is no carriage separate from the platform that can move gantry 410. Instead, platform 420 itself can be moved if desired. System 400 may be locked in the chosen position using four pins that can shunt the four wheels when the CT is in position. The four pins can be moved by hand or hydraulically. The bore diameter of gantry 410 is comparable to that of gantry 210—on the order of 60 cm—and thus used for brain, pediatric, and veterinary operations. FIG. 9A shows the patient not yet within the CT analysis zone of gantry 410. FIG. 9B shows that bed 50 can extend the patient into the CT analysis zone of gantry 410. In FIGS. 9C (perspective view) and 9D (top view), the patient's area of interest (e.g., brain) may be within the CT analysis zone of gantry 410 during the operation, with robotic arm assembly 440 and pivot arm 444 in the front left position. In FIGS. 9E (perspective view) and 9F (top view), the patient's area of interest (e.g., brain) may be within the CT analysis zone of gantry 410 during the operation, with robotic arm assembly 440 and pivot arm 444 in the front right position. An example of a CT device to be used within system 400 is Epica International's Pico™ CT scanner.

Figure 10A:
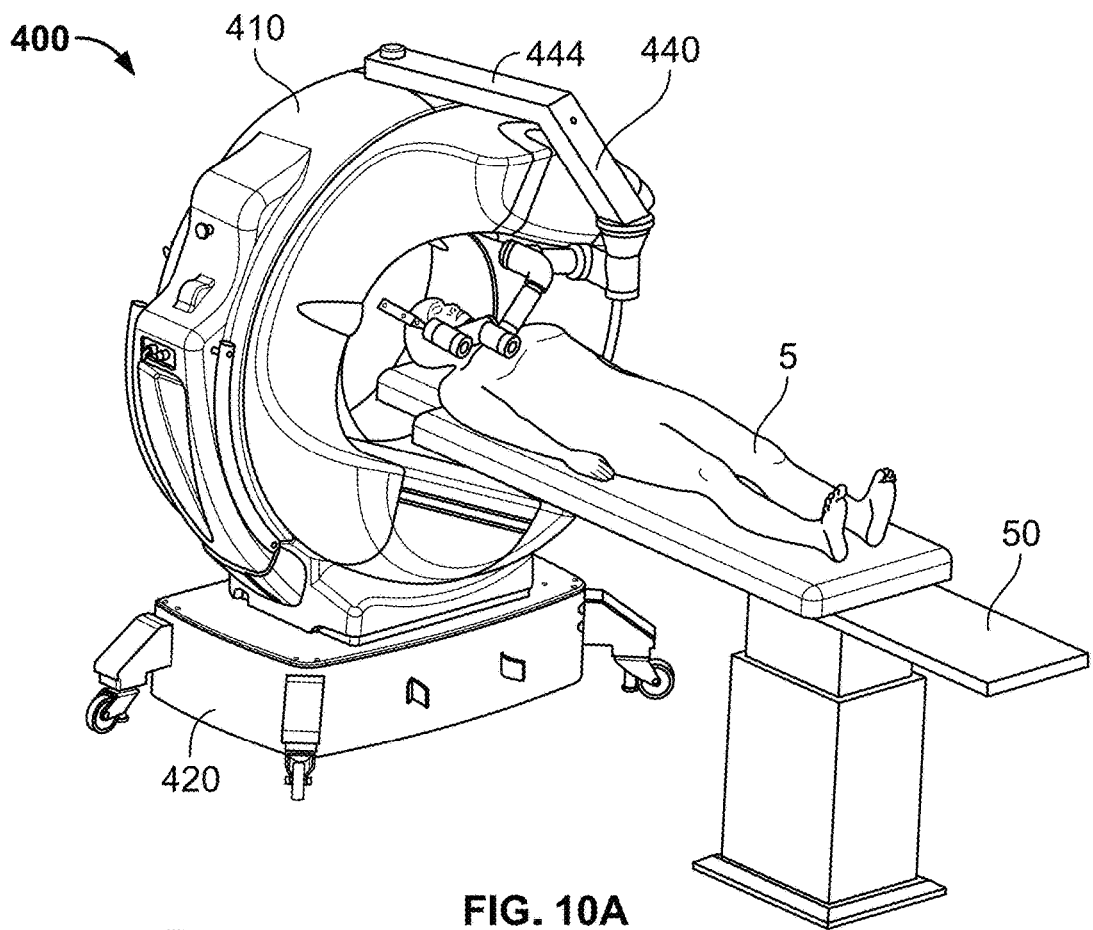
FIGS. 10A-10C show uses of the systems of FIGS. 9A-9F during robotic surgery, according to embodiments of the invention.
Figure 10B:
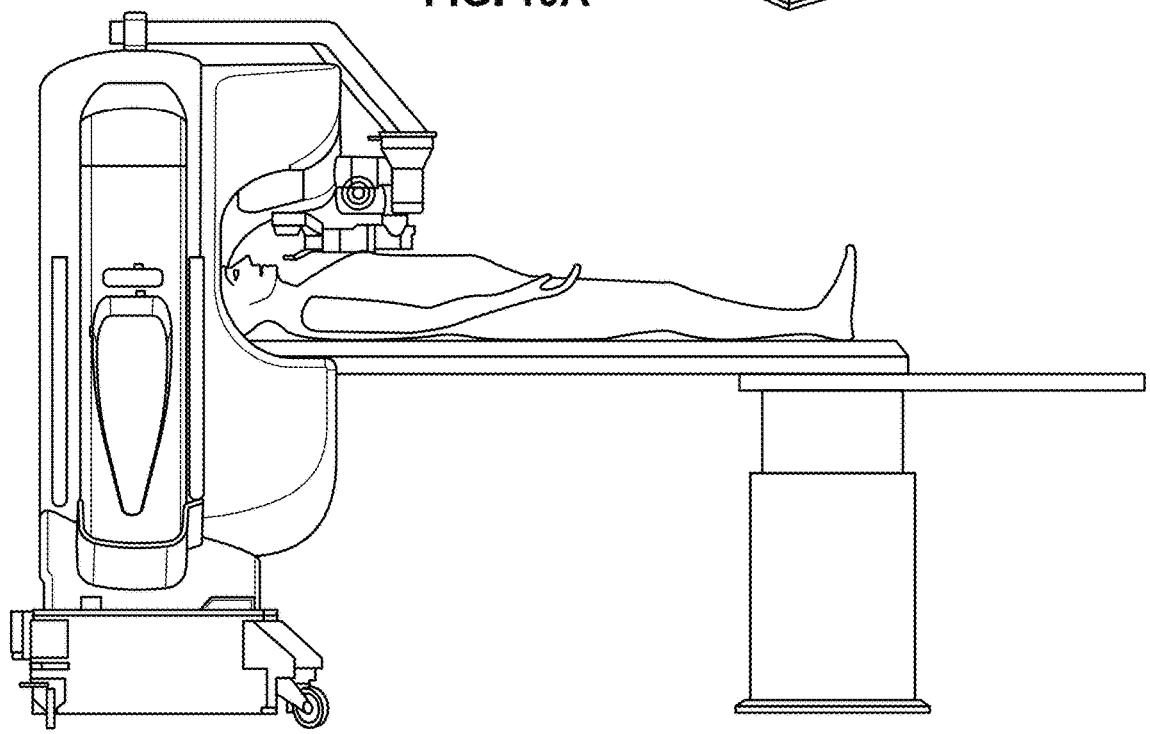
Figure 10C:
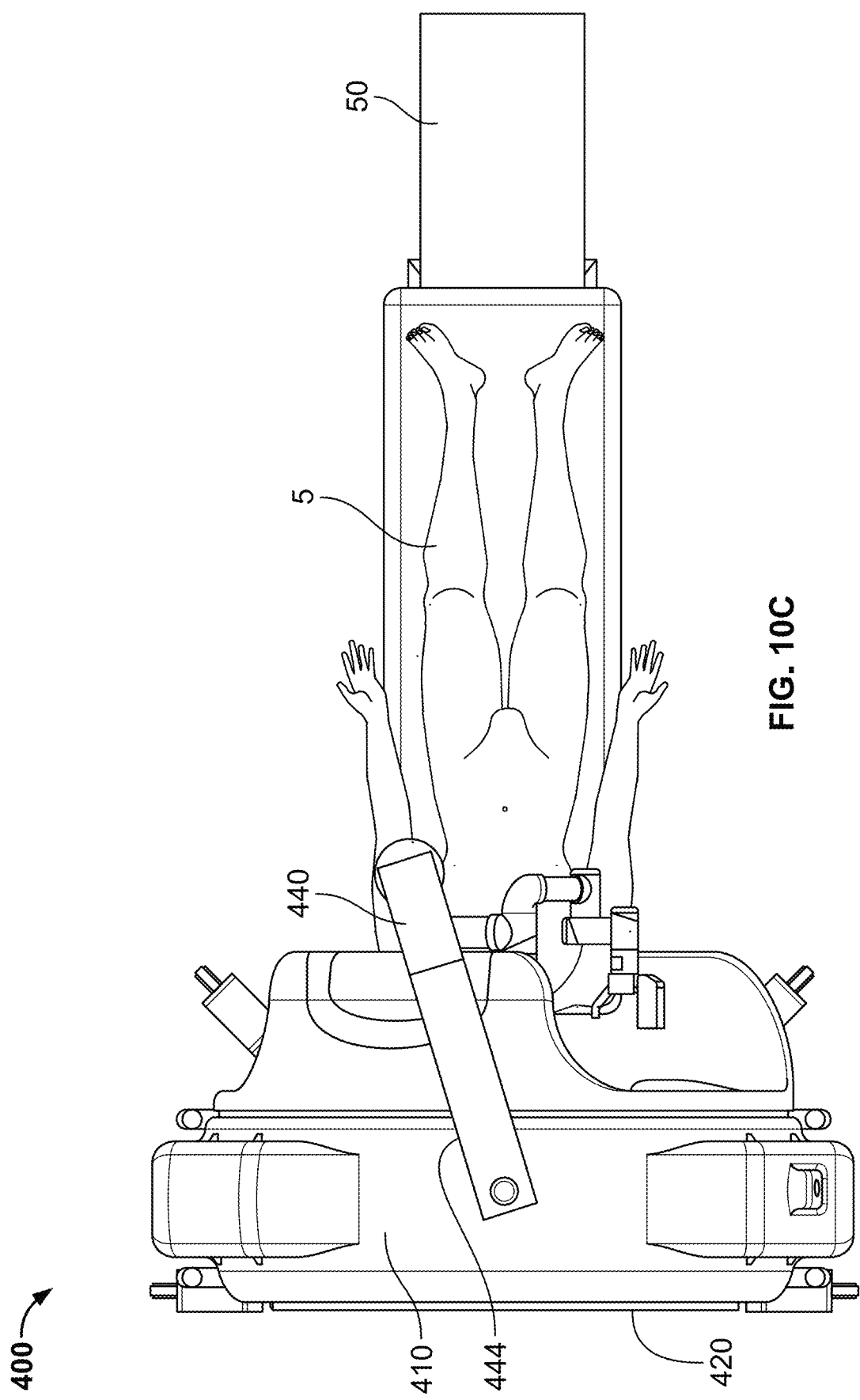

FIGS. 10A-10C show uses of system 400 during operations with robotic arm assembly 440 and pivot arm 444 again disposed on the front side of gantry 410, according to embodiments of the invention. The patient and table are located on the front side of gantry 410 rather than on the back side, as was shown in FIGS. 9A-9F. In FIGS. 10A (perspective view), 10B (side view), and 10C (top view), the patient's area of interest (e.g., neck and/or brain) may be within the CT analysis zone of gantry 410 during the operation. Robotic arm assembly 440 and pivot arm 444 can reach either side of the patient's body.

Accordingly, systems for performing robotic surgery have been described that provide increased access to surgical areas on a patient who is subject to CT scanning and/or imaging. The systems incorporate a CT gantry, a platform supporting the gantry, and a robotic arm assembly attached to the platform or gantry via a pivot arm. The pivot arm increases the surgical angles for the robotic arm. The pivot arm and associated motors may also help lock the robotic arm into position for more precise surgery.

The above discussion is meant to illustrate the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A system for performing robotic surgery on a patient disposed on a bed, comprising:
    a gantry comprising a computed tomography (CT) diagnostic device;
    a platform having an upper surface, wherein the gantry is attached to the upper surface of the platform and configured to slide along the upper surface of the platform via a first carriage to allow entry of at least part of the patient into the bore of the CT device; and
    a robotic arm assembly attached to the upper surface of the platform via a pivot arm and a second carriage, to allow the robotic arm assembly to slide along the platform to enable surgery to be performed on the patient, wherein the pivot arm extends substantially horizontally from a pivot point thereof and is substantially parallel to the upper surface of the platform, and wherein the robotic arm assembly extends upward from the pivot arm, which is below the bed, toward the patient to a position above the bed, thereby allowing access by the robotic arm to the patient's area of interest to perform surgery,
    wherein the pivot point is located in a center portion of the second carriage, in a direction transverse to a direction of movement of the gantry along the platform, to provide pivoting of the robotic arm assembly from a first side of the bed to a second side of the bed.

2. The system of claim 1, wherein the gantry comprises a movable x-ray source and movable x-ray detector.

* * * * *